(12) United States Patent
Orser et al.

(10) Patent No.: US 8,062,895 B2
(45) Date of Patent: *Nov. 22, 2011

(54) MISFOLDED PROTEIN SENSOR METHOD

(75) Inventors: Cindy Orser, Lafayette, CO (US); Anne Grosset, La Croix-de-Rozon (CH); Eugene A. Davidson, Washington, DC (US)

(73) Assignee: Adlyfe, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/726,941

(22) Filed: Mar. 18, 2010

(65) Prior Publication Data

US 2010/0267151 A1 Oct. 21, 2010

Related U.S. Application Data

(63) Continuation of application No. 10/494,906, filed as application No. PCT/US02/17212 on May 30, 2002, now Pat. No. 7,691,639.

(60) Provisional application No. 60/295,456, filed on May 31, 2001.

(51) Int. Cl.
  *G01N 33/52* (2006.01)
  *G01N 33/50* (2006.01)
  *G01N 33/00* (2006.01)
  *G01N 33/48* (2006.01)

(52) U.S. Cl. ......... 436/86; 436/166; 436/164; 530/350

(58) Field of Classification Search ............ 436/86, 436/164, 166; 435/7.1; 530/350, 418
See application file for complete search history.

(56) References Cited

U.S. PATENT DOCUMENTS

| 4,293,221 A * | 10/1981 | Kay et al. ............ 356/318 |
|---|---|---|
| 4,444,879 A | 4/1984 | Foster et al. |
| 5,565,186 A | 10/1996 | Prusiner et al. |
| 5,721,106 A | 2/1998 | Maggio et al. |
| 5,773,572 A | 6/1998 | Fishleigh et al. |
| 5,854,204 A | 12/1998 | Findeis et al. |
| 5,955,343 A | 9/1999 | Holmes et al. |
| 5,977,324 A * | 11/1999 | Prusiner et al. ............ 530/418 |
| 6,166,187 A | 12/2000 | Prusiner et al. |
| 6,214,565 B1 * | 4/2001 | Prusiner et al. ............ 435/7.1 |
| 6,290,954 B1 | 9/2001 | Prusiner et al. |
| 6,399,314 B1 | 6/2002 | Krishnamurthy |

(Continued)

FOREIGN PATENT DOCUMENTS

CA 2 443 929 A1 10/2002

(Continued)

OTHER PUBLICATIONS

U.S. Appl. No. 12/695,968, filed Jan. 28, 2010, Duan et al.

(Continued)

*Primary Examiner* — Christine T Mui
(74) *Attorney, Agent, or Firm* — Foley & Lardner LLP

(57) ABSTRACT

A catalytic conformational sensor method for detecting abnormal proteins and proteinaceous particles. The method is based on the interaction of a peptide fragment or probe with an abnormal proteinaceous particle. The interaction catalyzes the transformation of the probe to a predominately beta sheet conformation and allows the probe to bind the abnormal proteinaceous particle. This in turn, catalyzes the propagation of a signal associated with the test sample-bound probe. As a result signals can be propagated even from samples containing very low concentrations of abnormal proteinaceous particles. The peptide probes can be designed to bind to a desired peptide sequence or can even be based on dendrimer structure to control further aggregate propagation.

23 Claims, 31 Drawing Sheets

U.S. PATENT DOCUMENTS

| | | | |
|---|---|---|---|
| 6,498,017 | B2 | 12/2002 | Reisner et al. |
| 6,534,036 | B1 | 3/2003 | Collinge et al. |
| 6,600,017 | B1 | 7/2003 | Glabe et al. |
| 6,677,125 | B2 | 1/2004 | Prusiner et al. |
| 6,750,025 | B1 | 6/2004 | Hammond et al. |
| 7,166,471 | B2 | 1/2007 | Orser et al. |
| 7,691,639 | B2 | 4/2010 | Orser et al. |
| 2001/0001061 | A1 | 5/2001 | Prusiner et al. |
| 2002/0042121 | A1 | 4/2002 | Riesner et al. |
| 2003/0215880 | A1 | 11/2003 | Burton et al. |
| 2004/0052928 | A1 | 3/2004 | Gazit |
| 2004/0224365 | A1 | 11/2004 | Glabe et al. |
| 2004/0229280 | A1 | 11/2004 | Hammond et al. |
| 2005/0026165 | A1 | 2/2005 | Orser et al. |
| 2005/0112607 | A1 | 5/2005 | Bamdad et al. |
| 2005/0118645 | A1 | 6/2005 | Michelitsch et al. |
| 2005/0181998 | A1 | 8/2005 | Adessi et al. |
| 2005/0221404 | A1 | 10/2005 | Lane et al. |
| 2006/0035242 | A1 | 2/2006 | Michelitsch et al. |
| 2006/0057636 | A1 | 3/2006 | Heegaard et al. |
| 2006/0057671 | A1 | 3/2006 | Orser et al. |
| 2006/0078892 | A1 | 4/2006 | Hammond et al. |
| 2006/0178302 | A1 | 8/2006 | Krafft et al. |
| 2006/0235199 | A1 | 10/2006 | Mihara et al. |
| 2006/0275910 | A1 | 12/2006 | Orser et al. |
| 2008/0095706 | A1 | 4/2008 | Orser et al. |
| 2008/0171341 | A1 | 7/2008 | Orser et al. |
| 2009/0238754 | A1 | 9/2009 | Wegrzyn et al. |
| 2009/0274621 | A1 | 11/2009 | Wegrzyn et al. |

FOREIGN PATENT DOCUMENTS

| | | |
|---|---|---|
| JP | 2004-155688 A | 6/2004 |
| WO | WO 97/16728 A1 | 5/1997 |
| WO | WO 97/43649 | 11/1997 |
| WO | WO 98/37411 A1 | 8/1998 |
| WO | WO 99/41279 A | 8/1999 |
| WO | WO 00/02575 | 1/2000 |
| WO | WO 00/26238 A2 | 5/2000 |
| WO | WO 00/43791 | 7/2000 |
| WO | WO 00/69900 A2 | 11/2000 |
| WO | WO 01/07473 | 2/2001 |
| WO | WO 01/07479 | 2/2001 |
| WO | WO 01/14412 | 3/2001 |
| WO | WO 01/50134 A2 | 7/2001 |
| WO | WO 01/77687 A2 | 10/2001 |
| WO | WO 02/04604 A | 1/2002 |
| WO | WO 02/04954 A2 | 1/2002 |
| WO | WO 02/053723 A2 | 7/2002 |
| WO | WO 03/001881 A2 | 1/2003 |
| WO | WO 03/085086 | 10/2003 |
| WO | WO 2004/018511 | 3/2004 |
| WO | WO 2004/029072 A2 | 4/2004 |
| WO | WO 2005/010533 | 2/2005 |
| WO | WO 2005/016127 | 2/2005 |
| WO | WO 2006/088823 A2 | 8/2006 |

OTHER PUBLICATIONS

U.S. Appl. No. 11/884,316, filed Oct. 24, 2008, Orser et al.
Office Action dated Sep. 8, 2004, issued by the Examiner in U.S. Appl. No. 10/161,061, now U.S. Patent No. 7,166,471 (5 pgs.).
Office Action dated Feb. 23, 2005, issued by the Examiner in U.S. Appl. No. 10/161,061, now U.S. Patent No. 7,166,471 (7 pgs.).
Office Action dated Jun. 15, 2005, issued by the Examiner in U.S. Appl. No. 10/161,061, now U.S. Patent No. 7,166,471 (5 pgs.).
Office Action dated Sep. 27, 2005, issued by the Examiner in U.S. Appl. No. 10/161,061, now U.S. Patent No. 7,166,471 (8 pgs.).
Office Action dated Jan. 17, 2006, issued by the Examiner in U.S. Appl. No. 10/161,061, now U.S. Patent No. 7,166,471 (8 pgs.).
Office Action dated Apr. 5, 2007, issued by the Examiner in U.S. Appl. No. 10/728,246 (8 pgs.).
Office Action dated Apr. 13, 2007, issued by the Examiner in U.S. Appl. No. 11/030,300 (14 pgs.).
Office Action dated Oct. 14, 2008 issued by the Examiner in U.S. Appl. No. 11/030,300.
Office Action dated Mar. 18, 2009 issued by the Examiner in U.S. Appl. No. 11/030,300.
Hachiya et al., Biochemical and Biophysical Research Communications, 323:339-344 (2004), © Elsevier, Inc.
Tcherkasskaya et al. J. of Biomolecular Structure & Dynamics 21(3):353-365 (2003) © Adenine Press.
Fraser P E et al: "Conformation and fibrillogenesis of Alzheimer A-beta peptides with selected substitution of charged residues" Journal of Molecular Biology, London, GB, vol. 244, No. 1, 1994, pp. 64-73, XP002957211 ISSN:0022-2836.
Buschmann et al., "Detection of cattle-derived BSE prions using transgenic mice overexpressing bovine PrPC"; Archives of Virology, Supplement 16:75-86 (2000).
Koclsko et al.; "Cell-Free Formation of Protease-Resistant Prion Protein"; Nature, 370:471-474 (Aug. 11, 1994).
Lu et al. "Structural Determinants for Ligand-Receptor Conformational Selection in a Peptide G Protein-coupled Receptor," The Journal of Biological Chemistry 282:17921-17929 (2007).
Maxson et al.; "A solid-phase assay for identification of modulators of prion protein interactions"; Analytical Biochemistry, 323(1): 54-64 (Dec. 1, 2003).
Nicotera, P. "A Route for Prion Neuroinvasion," Neuron 31:345-348 (Aug. 16, 2001).
Office Action dated Dec. 4, 2007, issued by the Examiner in U.S. Appl. No. 10/728,246 (7 pgs.).
Office Action dated Dec. 21, 2007, issued by the Examiner in U.S. Appl. No. 11/030,300 (11 pgs.) (9 pgs.).
Ishii et al., "Fluorescence Studies of the Conformation of Pyrene-labeled Tropomyosin: Effects of F-actin and Myosin Subfragment 1," Biochemistry 24(23):6631-6638 (Nov. 1985) (Abstract Only).
Mihara et al. "Synthesis, Receptor Binding Activity and Fluorescence Property of Fluorescent Enkephalin Analogs Containing L-1-pyrenylalanine," Int. J. Pept Protein Res. 30(5):605-612 (Nov. 1987) (Abstract Only).
Ruiz et al., "Monomer and Excimer Fluorescence of Horse Plasma Gelsolin Labelled with N-(1-pyrenyl)iodoacetamide," Biochem Cell Biol 70(7):573-578 (Jul. 1992) (Abstract Only).
Office Action issued on Jun. 11, 2009, by the Examiner in U.S. Appl. No. 10/494,906 (US 2006/0275910).
Pillot et al., "The 118-135 Peptide of Human Prion Protein forms Amyloid Fibrils and Induces Liposome Function," J. Mol. Biol., vol. 274, pp. 381-393, 1997.
Pan et al., "Conversion of alpha-helices into beta-sheets features in the formation of the scrapie prion proteins," Biochemistry, vol. 90, pp. 10962-10966, Dec. 1993.
Graceffa et al., "The Excimer Fluorescense of Pyrene-labeled Tropomyosin," The Journal of Biological Chemistry, vol. 25, No. 23, pp. 11296-11300, 1980.
Grosset et al: "Rapid presymptomatic detection fo PrP<Sc> via conformationally responsive palindromic PrP peptides" Peptides, Elsevier, Amsterdam, US, vol. 26, No. 11, Nov. 2005, pp. 2193-2200, XP005137424 ISSN: 0196-9781.
Anantharamaiah, G.M., et al., "Studies of Synthethic Peptide Analogs of the Amphipathic Helix", J. Biol. Chem. vol. 260(18) pp. 10248-10255, 1985.
Anfinsen, C.B., "Principles that Govern the Folding of Protein Chains", Science, vol. 181(4096), pp. 223-230, 1973.
Baba, M., et al., "Aggregation of -Synuclein in Lewy Bodies of Sporadic Parkinson's Disease and Dementia with Lewy Bodies", Am. J. Patthology, vol. 152(4), pp. 879-885, 1998.
Baker, D., "A surprising simplicity to protein folding", Nature, vol. 405, pp. 39-42, 2000.
Booth, D.R., et al., "Instability, unfolding and aggregation of human lysozyme variants underlying amyloid fibrillogenesis", Nature, vol. 385, pp. 787-793, 1997.
Carrell, R.W. et al., "Conformational Disease", The Lancet, vol. 350, pp. 134-138, 1997.
Chiti, F., et al., "Designing conditions for in vitro formation of amyloid protofilaments and fibrisis", Proc. Natl. Acad. Sci. USA, vol. 96, pp. 3590-3594, 1999.
Chitnumsub et al., "The Nucleation of Monomeric Parallel Beta-Sheet-Like Structures and Their Self-Assembly in Aqueous Solution" Bioorganic & Medicinal Chemistry, vol. 7 (1), pp. 39-59, (1999).

Daura, X., et al., "Reversible Peptide Folding in Solution by Molecular Dynamics Simulation", J. Mol. Biol., vol. 280, pp. 925-932, 1998.
Dobson, C.M. et al., "Kinetic studies of protein folding using NMR spectroscopy", Nature Structural Biology Suppl: pp. 504-507, Jul. 1998.
Dobson, C.M., "Protein misfolding, evolution and disease", TIBS, vol. 24, pp. 329-332, 1999.
Dobson, C.M., "The structural basis of protein folding and its links with human disease", Phil. Trans. R. Soc. London B, vol. 356, pp. 133-145, 2001.
Wilson et al. "Conformational Transitions in Model Silk Peptides" Biophysical Journal 78 (5): 2690-2701 (May 2000).
Shaked et al. "A Protease-resistant Prion Protein Isoform is Present in Urine of Animals & Humans Affected with Prion Diseases," Journal of Biological Chemistry, vol. 276, No. 34, pp. 31479-31482, Aug. 24, 2001.
Pan, et al., "Conversion of alpha-helices into beta-sheets features in the formation of the scrapie prion proteins," Proc. of National Academy of Science, USA, vol. 90, pp. 10962-10966, 1993.
Isenman, D.E., et al., "The Structure and Function of Immunoglobulin Domains", Proc. Natl. Acad. Sci. USA, vol. 72(2), pp. 548-552, 1975.
Krawczak, M., et al., "Human Gene Mutation Database—A Biomedical Information and Research Resource", Human Mutation, vol. 15, pp. 45-51, 2000.
Lansbury, P.T., "Evolution of amyloid: What normal protein folding may tell us about fibrillogenesis and disease", Proc. Natl. Acad. Sci. USA, vol. 96, pp. 3342-3344, 1999.
Levy, E., et al., "Stroke In Icelandic Patients With Hereditary Amyloid Angiopathy Is Related to a Mutation In The Cystatin C Gene, An Inhibitor of Cysteine Proteases", J. Exp. Med., vol. 169, pp. 1771-1778, 1989.
Liao, Y-C.J., et al., "Human Prion Protein cDNA: Molecular Cloning, Chromosomal Mapping, and Biological Implications". Science, vol. 233, pp. 364-367, 1986.
MacPhee, C.E., et al., "Chemical Dissection and Reassembly of Amyloid Fibrils Formed by a Peptide Fragment of Transthyretin", J. Mol. Biol., vol. 297, pp. 1203-1215, 2000.
Matouschek, A., et al., "Mapping the transition state and pathway of protein folding by protein engineering", Nature, vol. 340, pp. 122-126, 1989.
Nguyen, J., et al., "Prion Protein Peptides Induce -Helix to -Sheet Conformational Transitions", Biochemistry, vol. 34, pp. 4186-4192, 1995.
Oesch, B., et al., "A Cellular Gene Encodes Scrapie PrP 27-30 Protein", Cell, vol. 40, pp. 735-746, 1985.
Perutz, M.F., "Glutamine repeats and neurodegenerative disease: molecular aspects", TIBS, vol. 24, pp. 58-63, 1999.
Prusiner, S.B., et al., "Prion Protein Biology", Cell 93:337-348, 1998.
Riordan, J.R., "Identification of the Cystic Fibrosis Gene: Cloning and Characterization of Complementary DNA", Science 245:1066-1073, 1989.
Salmona, M., et al., "Molecular determinants of the physicochemical properties of a critical prion protein region comprising residues 106-126", Biochemical Journal 342:207-214, 1999.
Schatzl, H.M., "Prion Protein Gene Variation Among Primates", J. Mot. Biol. 245:362-374, 1995.
Soto, C., "Protein misfolding and disease; protein refolding and therapy", FEBS Letters 498:204-207, 2001.
Speed, M.A., et al., "Specific aggregation of partially folded polypeptide chains: The molecular basis of inclusion body composition", Nature Biotechnology 14:1283-1287, 1996.
Speed, M.A., et al., "Polymerization Mechanism of Polypeptide Chain Aggregation", Biotechnology and Bioengineering 54(4):333-343, 1997.
Spillantini, M.G., "-Synuclein in filamentous inclusions of Lewy bodies from Parkinson's disease and dementia with Lewy bodies", Proc. Mad. Acad. Sci. USA 95:6469-6473, 1998.
Spillantini, M.G., "-Synuclein in Lewy bodies" Nature 388:839-840, 1997.
Stahl, N., et al., "Prions and prion proteins", The FASEB Journal 5:2799-2807, 1991.
Surewicz, W.K., et al., "Infrared spectroscopic evidence of conformational transitions of an atrial natriuretic peptide", Proc. Natl. Acad. Sci. USA 84:7028-7030, 1987.
Thomas, P.J., et al., "Defective protein folding as a basis of human disease", TIBS 20:456-459, 1995.
Westaway D., et al., "Distinct Prion Proteins in Short and Long Scrapie Incubation Period Mice", Cell 51:651-662, 1987.
Prior, R., et al., "Selective binding of Soluble A 1-40 and A 1-42 to a Subset of Senile Plaques", Am. J. Pathology, vol. 148(6), pp. 1740-1756, 1996.
Epstein, "Molecular Basis of the Neurodegenerative Disorders," New Eng. J. of Med., 340(25): 1970-1980, 1999.
Dobson, "The structural basis of protein folding and its links with human disease," Phil. Trans. R. Soc. London B, 356:133-145, 2001.
Nguyen et al: "Prion Protein Peptides Induce αHelix to β-Sheet Conformational Transitions" American Chemical Society, Biochemistry 1995, 34, 4186-4192; Departments of Neurology, Medicine, Pharmaceutical Chemistry, and Biochemistry and Biophysics, University of California, San Francisco, California 94143.
International Search Report issued on Aug. 22, 2006 in application No. PCT/US2004/40309 (corresponding to US 7,166,471).
International Search Report issued on Sep. 18, 2003 in application No. PCT/US2002/17212 (corresponding to US 7,691,639).
Tjernberg et al., Assembling amyloid fibrils from designed structures containing a significant amyloid β-peptide fragment, Biochem. J., 366:343-351, 2002.
Caughey et al., "Interactions and Conversions of Prion Protein Isoforms," Protein Science, pp. 139-169, Jan. 2001.
Notice of Allowance issued on Oct. 26, 2009 by the Examiner in U.S. Appl. No. 10/494,906 (US 7,691,639).
Office Action issued on Jul. 3, 2008 by the Examiner in U.S. Appl. No. 10/494,906 (US 7,691,639).
Office Action issued on Jan. 9, 2009 by the Examiner in U.S. Appl. No. 10/494,906 (US 7,691,639).
Office Action issued on Jan. 14, 2008 by the Examiner in U.S. Appl. No. 10/494,906 (US 7,691,639).
Office Action issued on Aug. 5, 2010 by the Examiner in U.S. Appl. No. 11/979,226 (US 2008/0171341).
Office Action issued on Dec. 16, 2009 by the Examiner in U.S. Appl. No. 11/979,226 (US 2008/0171341).
Office Action issued on Aug. 16, 2010 by the Examiner in U.S. Appl. No. 11/030,300 (US 2006/0057671).
Office Action issued on Nov. 16, 2009 by the Examiner in U.S. Appl. No. 11/030,300 (US 2006/0057671).
European Search Report issued on Jul. 4, 2011 in application No. 10188900.

* cited by examiner

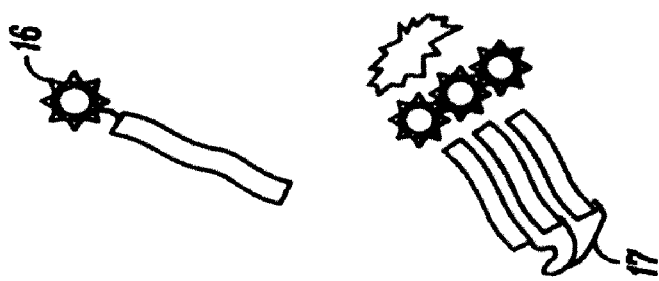
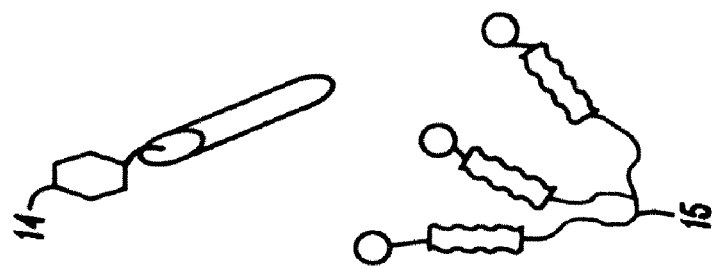
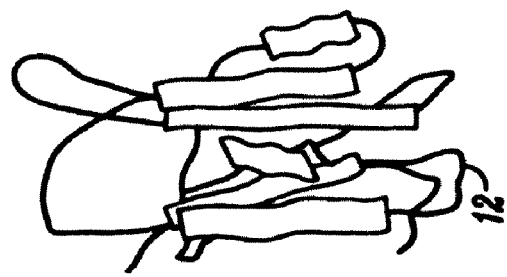
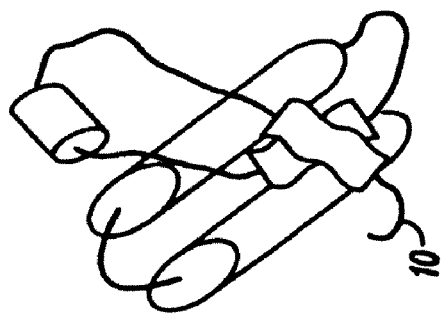
FIG. 1

| TEMPERATURE(°C) | 25°C | 50°C |
|---|---|---|
| pH 7 ALONE | RANDOM COIL | RANDOM COIL |
| pH 11 ALONE | ALPHA-HELIX | BETA-SHEET |
| pH 7 + pH 11 | BETA-SHEET | BETA-SHEET |
| pH 11 AT 25°C + pH 11 AT 50°C | RANDOM COIL | — |

*FIG. 5*

EU TEST RESULTS

| TEST EVALUATED | SENSITIVITY TRUE POSITIVE | SENSITIVITY TRUE NEGATIVE | DETECTION LIMIT* ^ |
|---|---|---|---|
| PRIONICS CHECK | 100% | 100% | $10^{-1}$ ~126 LD50/g |
| ENFER | 100% | 100% | $10^{-1.5}$ ~70 LD50/g |
| CEA | 100% | 100% | $10^{-2.5}$ ~7 LD50/g |
| E.G. &G. WALLAC | 70% | 90% | $10^{0}$ ~1259 LD50/g |

* MATERIAL USED TO PREPARE DILUTIONS WAS BOVINE NERVOUS TISSUE TITRATED IN MICE AT $10^{3.1}$ MOUSE i.c. LD50/g OF TISSUE (=1259 LD50/G)

^ AN INFECTIOUS DOSE IS DESIGNATED TO BE $10^5$ PrP MONOMERS PER BROWN ET AL. (1994) ANN. NEUROLOGY 35:513-529

*FIG. 12* -PRI

|        | 104       | 110     | 120              | 130              | 140      |              |
|--------|-----------|---------|------------------|------------------|----------|--------------|
| HUMAN    | KPKTNMKH | MAGAAAAGAVVGGLGGYMLGSAMSRP | I | HF | (SEQ ID NO: 1) |
| HAMSTER  | KPKTNMKH | MAGAAAAGAVVGGLGGYMLGSAMSRP | M | HF | (SEQ ID NO: 2) |
| MOUSE    | KPKTNLKH | VAGAAAAGAVVGGLGGYMLGSAMSRP | M | HF | (SEQ ID NO: 3) |
| BOVINE   | KPKTNMKH | VAGAAAAGAVVGGLGGYMLGSAMSRP | P | HF | (SEQ ID NO: 4) |
| ELK      | KPKTNMKH | VAGAAAAGAVVGGLGGYMLGSAMSRP | L | HF | (SEQ ID NO: 5) |
| DEER     | KPKTNMKH | VAGAAAAGAVVGGLGGYMLGSAMSRP | L | HF | (SEQ ID NO: 6) |

FIG. 13

19-mer  *KPKTNMKH MAGAAAAGAVV    (SEQ ID NO: 7)
14-mer  *MKH MAGAAAAGAVV         (SEQ ID NO: 8)

lys-pro-lys-thr-asn-met-lys-his-met-ala-gly-ala-ala-ala-ala-gly-ala-val-val (SEQ ID NO: 7)

FIG. 14

SEQUENCE LISTING

<160> NUMBER OF SEQ ID NOS: 10

<210> SEQ ID NO 1
<211> LENGTH: 38
<212> TYPE: PRT
<213> ORGANISM: Homo sapiens

<400> SEQUENCE: 1

Lys Pro Lys Thr Asn Met Lys His Met Ala Gly Ala Ala Ala Ala Gly
 1               5                  10                  15

Ala Val Val Gly Gly Leu Gly Gly Tyr Met Leu Gly Ser Ala Met Ser
            20                  25                  30

Arg Pro Ile Ile His Phe
        35

<210> SEQ ID NO 2
<211> LENGTH: 38
<212> TYPE: PRT
<213> ORGANISM: Cricetus sp.

<400> SEQUENCE: 2

Lys Pro Lys Thr Asn Met Lys His Met Ala Gly Ala Ala Ala Ala Gly
 1               5                  10                  15

Ala Val Val Gly Gly Leu Gly Gly Tyr Met Leu Gly Ser Ala Met Ser
            20                  25                  30

Arg Pro Met Met His Phe
        35

<210> SEQ ID NO 3
<211> LENGTH: 38
<212> TYPE: PRT
<213> ORGANISM: Mus sp.

<400> SEQUENCE: 3

Lys Pro Lys Thr Asn Leu Lys His Val Ala Gly Ala Ala Ala Ala Gly
 1               5                  10                  15

Ala Val Val Gly Gly Leu Gly Gly Tyr Met Leu Gly Ser Ala Met Ser
            20                  25                  30

Arg Pro Met Ile His Phe
        35

<210> SEQ ID NO 4
<211> LENGTH: 38
<212> TYPE: PRT
<213> ORGANISM: Bos sp.

<400> SEQUENCE: 4

Lys Pro Lys Thr Asn Met Lys His Val Ala Gly Ala Ala Ala Ala Gly
 1               5                  10                  15

Ala Val Val Gly Gly Leu Gly Gly Tyr Met Leu Gly Ser Ala Met Ser
            20                  25                  30

Arg Pro Pro Ile His Phe
        35

<210> SEQ ID NO 5
<211> LENGTH: 38
<212> TYPE: PRT
<213> ORGANISM: Cervus sp.

<400> SEQUENCE: 5

```
Lys Pro Lys Thr Asn Met Lys His Val Ala Gly Ala Ala Ala Ala Gly
 1               5                  10                  15

Ala Val Val Gly Gly Leu Gly Gly Tyr Met Leu Gly Ser Ala Met Ser
            20                  25                  30

Arg Pro Leu Ile His Phe
                35

<210> SEQ ID NO 6
<211> LENGTH: 38
<212> TYPE: PRT
<213> ORGANISM: Odocoileus sp.

<400> SEQUENCE: 6

Lys Pro Lys Thr Asn Met Lys His Val Ala Gly Ala Ala Ala Ala Gly
 1               5                  10                  15

Ala Val Val Gly Gly Leu Gly Gly Tyr Met Leu Gly Ser Ala Met Ser
            20                  25                  30

Arg Pro Leu Ile His Phe
                35

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Pro Lys Thr Asn Met Lys His Met Ala Gly Ala Ala Ala Ala Gly
 1               5                  10                  15

Ala Val Val

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Lys His Met Ala Gly Ala Ala Ala Ala Gly Ala Val Val
 1               5                  10

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Pro Lys Thr Asn Met Lys His Met Ala Gly Ala Ala Ala Ala Gly
 1               5                  10                  15

Ala Val Val

<210> SEQ ID NO 10
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 10

Val Val Ala Gly Ala Ala Ala Gly Ala Val His Lys Leu Asn Thr
 1               5                  10                  15

Lys Pro Lys Leu Lys His Val Ala Gly Ala Ala Ala Gly Ala Val
            20                  25                  30

Val
```

MISFOLDED PROTEIN SENSOR METHOD

This document claims priority of U.S. provisional patent application Ser. No. 60/295,456 filed on May 31, 2001, with respect to subject matter therein; said provisional application fully being incorporated herein.

BACKGROUND

1. Field of the Invention

This invention relates generally to a catalytic conformational sensor method and application of such method for detecting proteins and proteinaceous particles; and more particularly to detecting misfolded or disease-associated proteins and proteinaceous particles.

2. Related Art

The present invention detects misfolded or abnormal conformations of proteins or peptides such as those contributing to "folding diseases". The "folding diseases" are characterized by proteins with destabilizing conformers which tend to aggregate and eventually form toxic plaques in brain and other tissue. See Bucciantini, M., et al. (2002) *Inherent Toxicity of Aggregates Implies a Common Mechanism for Protein Misfolding Diseases*. Nature 416:507-511.

These "folding diseases" can be hard to diagnose since the disease symptoms may be latent where the aggregates are slowly building up over time and go through stages of increased aggregation leading to fibril formation and eventual plaque deposition leading to impairment of cellular viability. Such misfolding of peptides and aggregate formation is believed to play a key role in Alzheimer's disease where beta-amyloid protein (or A beta, a 39-42 residue peptide) forms fibrillar deposits upon a conformer change; Huntington's disease where insoluble protein aggregates are formed by expansion of poly-glutamine tracts in the N-terminus of huntingtin (Htt), an antiapoptotic neuronal protein; and non-infectious cancers such as in cases where tumor-associated cell surface NADH oxidase (tNOX) has prion-like properties such as proteinase$^R$, ability to form amyloid filaments and the ability to convert the normal NOX protein into tNOX. See Kelker, et al. *Biochemistry* (2001) 40:7351-7354. for more information on tNOX.

The present invention, however, is not limited to the detection of proteins or peptides in folding-disease or infectious samples. It also includes detection of proteinaceous particles such as prions. Prions are small proteinaceous particles with no nucleic acids, thus are resistant to most nucleic-acid modifying procedures and proteases. The normal prion (PrP) protein is a cell-surface metalloglyroprotein that is mostly an alpha-helix and loop structure as shown in FIG. 8, and is usually expressed in the central nervous and lymph systems. It's proposed function is that of an antioxidant and cellular homeostasis.

The abnormal form of the PrP, however, is a conformer which is resistant to proteases and is predominantly beta-sheet in its secondary structure as shown in FIG. 9. It is believed that this conformational change in secondary structure is what leads to the aggregate and eventual neurotoxic plaque deposition in the prion-disease process.

The abnormal prion are infectious particles that play key roles in the transmission of several diseases such as Creutzfeldt-Jakob syndrome, chronic wasting disease (CWD), nvCJD, transmissible spongiform encephalopathy (TSE), Mad Cow disease (BSE) and scrapie a neurological disorder in sheep and goats[1].

[1] Clayton Thomas, *Tabor's Cyclopedic Medical Dictionary* (Phil F. A. Davis Company, 1989), at 1485.

Diseases caused by prions can be hard to diagnose since the disease may be latent where the infection is dormant, or may even be subclinical where abnormal prion is demonstrable but the disease remains an acute or chronic symptomless infection. Moreover, normal homologues of a prion-associated protein exist in the brains of uninfected organisms, further complicating detection.[2] Prions associate with a protein referred to as PrP 27-30, a 28 kdalton hydrophobic glycoprotein, that polymerizes (aggregates) into rod-like filaments, plaques of which are found in infected brains. The normal protein homologue differs from prions in that it is readily degradable as opposed to prions which are highly resistant to proteases. Some theorists believe that prions may contain extremely small amounts of highly infectious nucleic acid, undetectable by conventional assay methods.[3] As a result, many current techniques used to detect the presence of prion-related infections rely on the gross morphology changes in the brain and immunochemistry techniques that are generally applied only after symptoms have already manifest themselves. Many of the current detection methods rely on antibody-based assays or affinity chromatography using brain tissue from dead animals and in some cases capillary immunoelectrophoresis using blood samples.

[2] Ivan Roitt, et al., *Immunology* (Mosby—Year Book Europe Limited, 1993), at 15.1.

[3] Benjamin Lewin, *Genes IV* (Oxford Univ. Press, New York, 1990), at 108.

The following is an evaluation of current detection methods.

Brain Tissue Sampling. Cross-sections of brain can be used to examine and monitor gross morphology changes indicative of disease states such as the appearance of spongiform in the brain, in addition to immunohistochemistry techniques such as antibody-based assays or affinity chromatography which can detect disease-specific prion deposits. These techniques are used for a conclusive bovine spongiform encephalopathy (BSE) diagnosis after slaughter of animals displaying clinical symptoms. Drawbacks of tissue sampling include belated detection that is possible only after symptoms appear, necessary slaughter of affected animals, and results that takes days to weeks to complete.

Prionic-Check also requires liquified-brain tissue for use with a novel antibody under the Western Blot technique. This test is as reliable as the immunochemistry technique and is more rapid, yielding results in six to seven hours, but shares the drawbacks of the six-month lag time between PrP$^s$ accumulation (responsible for the gross morphology changes) in the brain and the display of clinical symptoms, along with the need for slaughter of the animal to obtain a sample.

Tonsillar Biopsy Sampling. Though quite accurate, it requires surgical intervention and the requisite days to weeks to obtain results.

Body Fluids: Blood and Cerebrospinal Sampling. As in the above detection methods, results are not immediate Electrospray ionization mass spectrometry (ESI-MS), nuclear magnetic resonance NMR, circular dichroism (CD) and other non-amplified structural techniques. All of these techniques require a large amount of infectious sample, and have the disadvantage of requiring off-site testing or a large financial investment in equipment.

The following is a survey of currently approved and certified European Union (EU) prion-detection tests.

Prionics—in Switzerland. The test involves Western blot of monoclonal antibodies (MABs) to detect PrP in brain tissue from dead animals in seven to eight hours.

Enfer Scientific—in Ireland. The test involves ELISA-based testing on spinal cord tissue from dead animals in under four hours.

CEA—in France. The test involves a sandwich immunoassay using two monoclonals on brain tissue collected after death in under twenty-four hours.

The EU Commission's evaluation protocol has sensitivity, specificity and detection limits and titre. The sensitivity of a test is the proportion of infected reference animals that test positive in the assay. It previously used 300 samples from individual animals to assess this element. The specificity of a test is the proportion of uninfected reference animals that test negative in the assay. Previously used 1,000 samples from individual animals for this purpose. In order to test detection limits, various dilutions ranging from $10^0$ to $10^{-5}$ of positive brain homogenate were used. A table showing an evaluation of EU test results is shown in FIG. 12. Even with high degrees of sensitivity and specificity, however, the fact remains that these tests must be performed post-mortem and require working with large amounts of highly infectious biohazard materials.

The Center for Disease Control (CDC) classifies prions as Risk Group 2 agents requiring Biosafety Level 2 (BSL2) containment. As a result many of the above operations are carried out under BSL2 physical containment with elevated safety practices more typical of a BSL3 lab. Prions can be inactivated by fresh household bleach, 1 molar NaOH, 4 molar guanidine reagents, or phenol followed by 4.5 hours of autoclaving at 132° C. Procedures involving brain tissue from human patients with neurological degenerative disorders pose special challenges and should be handled with the same precautions as HIV+ human tissue. Thus, working with large amounts of such biohazardous materials can be an obstacle to quick and simple testing of mass quantities or assembly-line samples as well as cumbersome even for small applications.

In addition to working with relatively large amounts of biohazardous materials and taking several hours to weeks for detection, many of the prior art methods have the added difficulty that they are performed post mortem.

As can now be seen, the related art remains subject to significant problems, and the efforts outlined above—although praiseworthy—have left room for considerable refinement. The present invention introduces such refinement.

SUMMARY OF THE DISCLOSURE

The present invention is based on the interaction between low concentration levels of abnormal proteinaceous particles and a peptide fragment or probe to induce transformation and propagation of the probe bound to the abnormal proteinaceous particles initially present within a test sample. Thus, in a preferred embodiment, infectious levels of a test sample can be propagated even from low concentrations.

The present invention uses catalytic propagation to exploit conformational changes in proteins associated with a particular disease process, such as transmissible spongiform encephalopathy (TSE). Catalytic propagation basically amplifies the number of existing protein fragments causing aggregates to form. The aggregates of conformationally changed protein fragments are then easily detected using common analytical techniques.

As a result, the present invention allows testing to be done using rapid and cost-effective analytical techniques, even on, heretofore difficult to detect, small sample sizes and is widely applicable to tissues and body fluids other than those found in brain. Results of the present invention can easily and immediately interpreted using familiar analytical instrumentation. Additionally, the present invention can amplify a weak signal, thus can be successfully applied to small or weak samples such as those associated with body fluids; thereby opening the door to analysis of tissues and fluids for the elusive diseases discussed above. Moreover, this allows the method to be relatively noninvasive in that it does not need to be performed post-mortem; and because it does not need to be performed post-mortem it can be applied to presymptomatically.

The foregoing may be a description or definition of the first facet or aspect of the present invention in its broadest or most general terms. Even in such general or broad form, however, as can now be seen the first aspect of the invention resolves the previously outlined problems of the prior art.

Because the present invention allows detection using samples with very low levels of infectious agents and involves amplifying a peptide probe as opposed to a whole potentially infectious protein, many of the previous biohazard-handling concerns are reduced.

Now turning to another of the independent facets or aspects of the invention: in preferred embodiments of this facet, the peptide probes are designed for the detection of a desired sequence and so have adaptable levels of selectivity and specificity built into the method. Also, intrinsic optical fluors such as pyrene can be designed into the peptide probe allowing simple, single step optical detection of the abnormal proteinaceous particles.

All of the foregoing operational principles and advantages of the present invention will be more fully appreciated upon consideration of the following detailed description, with reference to the appended drawings, of which:

BRIEF DESCRIPTION OF THE DRAWINGS

FIG. 1 is a pictoral representation of conformers of transmissible spongiform encephalopathies (TSE) and probes in the form of labeled peptides and labeled dendrimers;

FIG. 2 is a pictoral representation of TSE protein detection schema;

FIG. 3 is a graph showing the conformational changes associated with a poly-L-lysine test peptide using circular dichroism;

FIG. 4 is a graph comparing the circular dichroism results of the poly-L-lysine test peptide at different temperatures and pH;

FIG. 5 is a table comparing the circular dichroism results of the poly-L-lysine test peptide at different temperatures and pH;

FIG. 6 is a graph of data for fluorescence resonance energy transfer (FRET) experiments for proximal and distal locations in an α-helical bundle structure undergoing conformational change;

FIG. 7 is a graph of the driving force necessary to overcome the energy difference between two different FIG. 8 is a structural diagram of a normal PcP protein, a cell-surface metallo-glycoprotein that is expressed in the central nervous and lymphatic systems, and that is characterized as having mostly an alpha-helix and loop structure;

FIG. 9 is a structural diagram of the PcP protein that has shifted to a predominately beta structure in which it is likely for form aggregates and neurotoxic fibrils eventually leading to plaque deposition;

FIG. 10 is a pictoral representation of amplification of signal and propagation of conformational change without increased aggregation by the addition of dendrimers of the invention to a test sample;

FIG. 12 is a table evaluating the current prior art in European Union certified prion-diagnostic tests FIG. 13 is a comparison showing selected PrP sequences among six different species;

FIG. 14 shows peptide sequences for the synthetic peptide probes Seq. 19 and Seq. 14 of this invention;

FIG. 15 is a graph of fluorescence detection experimental results showing the effects of peptide concentration;

FIG. 16 is a graph of fluorescence detection experimental results showing the effects of peptide concentration likely showing excimer emission at approximately 460 nanometers (nm);

FIG. 17 is a graph of fluorescence detection experimental results showing pyrene's excitation of fluorescence;

FIG. 18 is a graph of fluorescence detection experimental results showing pyrene's excitation spectra for fluorescence at 398 and approximately 460 nm;

FIG. 19 is a graph comparing the circular dichroism results of several peptides ranging in concentration from 20 to 100 milli Molar (mM) under varying buffer conditions;

FIG. 20 is a graph comparing the circular dichroism results of several peptides including the synthetic peptides of Seq. 19 and Seq. 14 under varying buffer conditions;

FIG. 21 shows experimental results of the conformational lability of the synthetic peptides. FIG. 21*a* on the left shows that Seq. 14 assumes a beta-sheet conformer while the longer analog, Seq. 19 remains coiled. FIG. 21*b* on the right shows that addition of Seq. 14 to Seq. 19 initiates a phase shift to beta-sheet form;

FIG. 22 is a conceptual illustration of a comparison of where Seq. 19 and Seq. 14 overlap in structure;

FIG. 23 is a graph of experimental results showing that peptides can self-associate;

FIG. 24 is a graph of fluorescence data showing the efficiency of excimer formation under low concentrations;

FIG. 25 is a graph of fluorescence experimental results showing the effect of nuclei on self-association due to catalytic conformational transition;

FIG. 26 contains two graphs of fluorescence experimental results showing the interaction of Seq. 19 and Seq. 14 at different ratios; wherein FIG. 26*a* on the left shows a 1:1 mixture and FIG. 26*b* on the right shows a 100:1 mixture;

FIG. 27 contains four graphs of fluorescence experimental results showing the effect of nuclei on self-association. FIGS. 27*a, b, c* and *d* show the results at 24 hours, 48 hours, 144 hours and 336 hours, respectively;

FIG. 28 is a graph of fluorescence experimental results showing the effect of nuclei on self-association due to catalytic conformational transition at 1 hour in FIG. 28*a* on the left and at 150 hours in FIG. 28*b* on the right;

FIG. 29 shows peptide sequences for a generalized dendrimer structure of this invention;

FIG. 30 shows a peptide sequence for a preferred embodiment of a specific dendrimer structure of this invention;

FIG. 31 is a conceptual diagram of an experimental device; and

FIG. 32 is a system diagram of preferred embodiments of the invention.

DETAILED DESCRIPTION OF THE PREFERRED EMBODIMENTS

It is to be understood that the invention is not limited to the examples described herein. All technical and scientific terms used herein have meanings as commonly understood by one of ordinary skill in the art unless otherwise defined. All publications referred to herein are wholly incorporated by reference to describe methods and materials for implementing aspects of the invention.

The present invention detects the presence of abnormal proteins and proteinaceous particles based on a method that utilizes catalytic propagation. Upon interaction of a sample, containing abnormal proteins or proteinaceous particles, with a peptide probe of the invention, the peptide probe undergoes conformational changes resulting in the formation of aggregates. The addition of the abnormal proteins and proteinaceous particles catalyzes the formation of the aggregates and causes further propagation of this conformational transition. The resulting aggregates are then easily detected using common analytical instrumentation and techniques.

The abnormal proteins and proteinaceous particles on which the invention focuses are proteins, protein based chemical structures such as prions and protein subunits such as peptides that are capable of conformational changes that lead to the formation of aggregates and ultimately to disease states.

These proteins and proteinaceous particles form aggregates by shifting from a monomeric to a multimeric state. The shift from one distinct state to the other requires a driving force that is commensurate with the energetic difference between the two conformational states as shown in FIG. 7.

A preferred example of such proteinaceous particles is that of a prion protein. Prions can exist in one of two distinct conformations characterized by having a secondary protein structure that is either predominately alpha-helical or predominately beta-sheet; where the predominately beta-sheet conformation has a much higher preference to exist in a multimeric state. As a result, predominately beta-sheet (or beta rich) secondary structure is more typical of abnormally folded or disease-causing proteinaceous particles since their preference to aggregate is likely to be disruptive in an in vivo environment.

FIG. 1 shows illustrations of both the alpha-helical monomer 10 and the beta-sheet dimer 12 forms of a TSE conformer (or alternative secondary structure). Research has shown that the normal wild-type (wt) form of prion protein ($PrP^{c}$) prefers a monomeric state, while the abnormal, disease-causing form ($PrP^{Sc}$) more readily takes on a multimeric state.[4]

[4] Fred E. Cohen, et al., *Pathologic Conformations of Prion Proteins* (Annu. Rev. Biochem. 1998) 67: 793-819.

This distinction between the secondary structure of the normal form of prion protein and the abnormal form as well as its propensity to cause aggregation is exploited in the present invention to allow detection of the abnormal form even in samples with very low levels of infectious abnormal protein.

The mechanism of the invention is shown in a schematic in FIG. 2. The top row of the schematic shows an example of an unknown sample of TSE protein represented as containing beta-sheets 12. The beta-sheets are then disaggregated by subjecting the sample to commonly known disaggregation methods such as sonication. This is followed by the addition of labeled peptide probes 14 which are allowed to bind to the sample 12. Presence of the beta-sheet conformation in the sample 12 induces the peptide probes to also shift to beta-sheet formation 16. In this manner the transition to beta-sheet is propagated among the peptide probes 14 thereby causing new aggregates 18 to form. The resulting transition to a predominately beta-sheet form and amplified aggregate formation can then easily be detected using common analytical techniques such as light scattering and circular dichroism (CD); and in a particularly preferred embodiment where the peptide probe is fluorescent labeled, fluorescence detection instrumentation can also be used.

Figure 2:
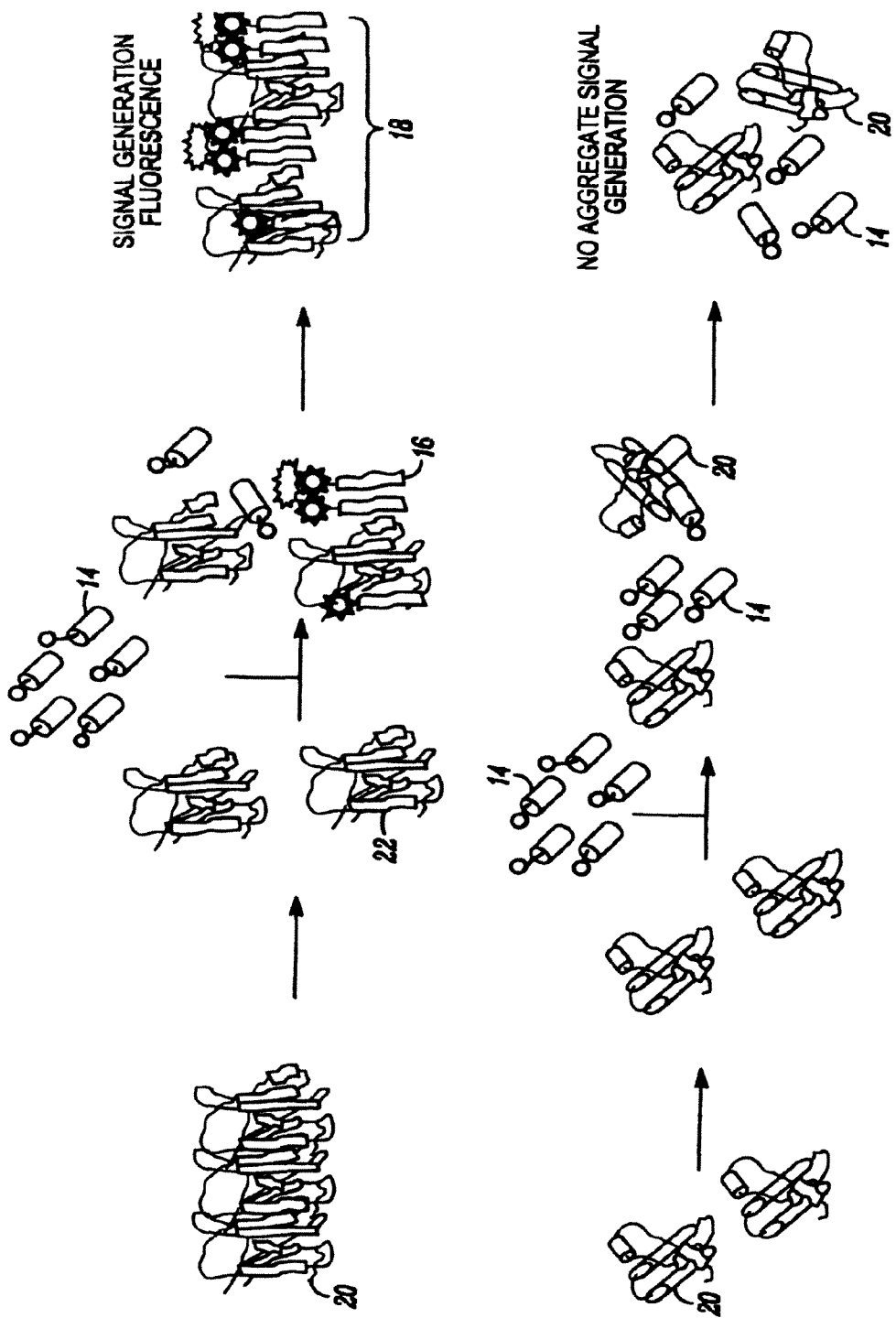
Figure 3:
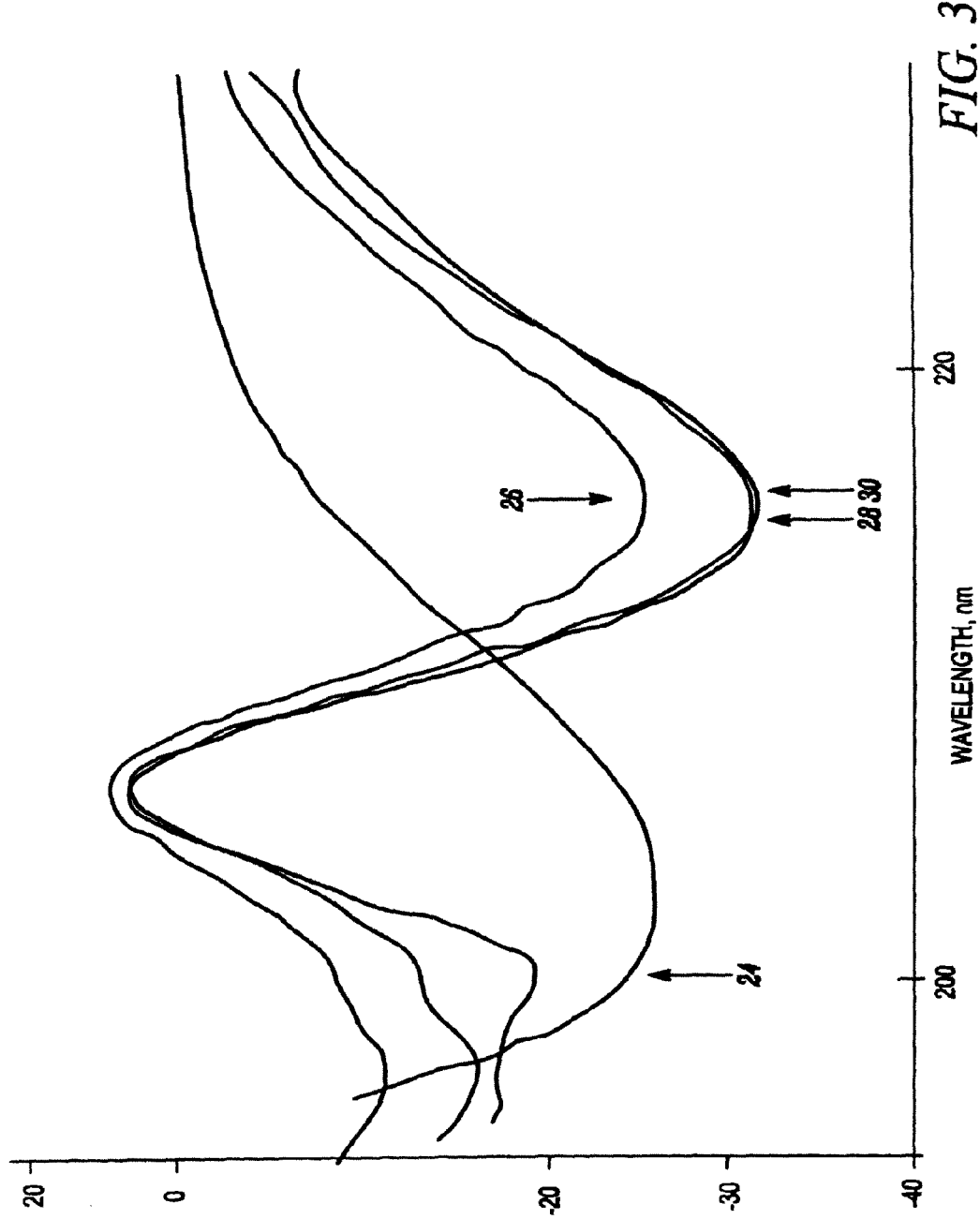

The bottom row of FIG. 2 shows an alternative example in which the unknown sample of TSE protein is represented in its normal alpha-helical form 10. For consistency, the sample is subjected to the same disaggregation process described above. Upon addition of the labeled peptide probes 14, neither a transition to beta-sheet form nor binding to the unknown samples occurs. As a result, there is no aggregate fluorescence signal in the case of a labaled peptide probe as well as no detection of aggregate formation by other analytical tools. Based on this schematic, unknown samples can be tested for the presence or absence of such abnormal protein conformations or sequences.

A preferred embodiment of the invention involves the following basic procedures. Peptide probes 14 are selected in order to be added to an unknown or test sample 20 at a later stage in the process. The peptide probes 14 are preferably proteins or peptide sequences that have secondary structures of predominately alpha-helix or random coil. In a particularly preferred embodiment, the peptide probes 14 are peptide fragments consisting of a helix-loop-helix structure as found in lysine. In another particularly preferred embodiment, the peptide probes can be made of a peptide sequence chosen from wild-type (wt) TSE, from a desired species-specific TSE peptide sequence, or even from a selectively mutated TSE sequence that has been mutated in such a manner as to render it destabilized and noninfectious. Additionally, extrinsic fluors such as pyrene can be added or designed into the peptide probe to allow detection of anticipated conformational changes using common fluorescence detection techniques.

Once a peptide probe 14 is selected, it is added to a test sample 20. Prior to the addition of the peptide probe 14, however, it is preferred to have the sample 20 subjected to disaggregation techniques commonly known in the art, such as sonication. The disaggregation step allows any potentially aggregated sample material 20 to break apart so that these disaggregated sample materials 22 are more free to recombine with the newly introduced peptide probes 14; thereby facilitating the anticipated catalytic propagation.

After the test sample 20 or disaggregated test sample 22 is allowed to interact with the peptide probes 14. The resulting mixture is then subjected to analytical methods commonly known in the art for the detection of aggregates and to fluorescence measurements in cases where fluorescent peptide probes 14 are used.

Unknown or test samples 20 containing any dominant beta-sheet formation characteristic of abnormally folded or disease-causing proteins results in an increase in beta-sheet formation and consequently aggregate formation in the final mixture containing both the test sample 20 and the peptide probes 14. Conversely, unknown or test samples 20 which lack a predominantly beta-sheet secondary structure will neither catalyze a transition to beta-sheet structure 16 nor will propagate the formation of aggregates 18.

One of ordinary skill in the art can appreciate that the means by which the initial conformational change can be triggered in the test samples 20 can be varied as described in the following examples. The binding of a metal ligand could direct a change in the protein scaffolding and favor aggregation. The expression or cleavage of different peptide sequences can promote advanced aggregation leading to fibril and plaque formation. Genetic point mutations can also alter the relative energy levels required of the two distinct conformations, resulting in midpoint shifts in structural transitions. Furthermore, an increase in concentration levels could be sufficient to favor the conformational transition. Regardless of the initial trigger mechanism, however, the disease process in many of the abnormal protein conformations such as in prion-related diseases always involves the catalytic propagation of the abnormal conformation, resulting in transformation of the previously normal protein.

One of ordinary skill in the art can also appreciate that there are many common protein aggregate detection techniques many of which are based on optical measurements. These optical detection techniques include, but are not limited to, light scattering, or hydrophobicity detection using extrinsic fluors such as 1-anilino-8-napthalene sulfonate (ANS) or Congo Red stain, fluorescence proximity probes on the peptide fragments, including fluorescence resonance energy transfer (FRET) & quenching of intrinsic tryptophan fluorescence through either conformational change of monomer or binding at interface in alpha-beta heterodimer; the N-terminal loop region is particularly interesting in this regard selective binding to target protein, circular dichroism (CD) monitoring of actual conformation, nuclear magnetic resonance (NMR). Other detection techniques include equilibrium ultracentrifugation or size-exclusion chromotography at the aggregation stage as well as other structural techniques. Examples and explanations of these methods can be found in Freifelder, David. *Physical Biochemistry: Applications to Biochemistry and Molecular Biology*, (W. H. Freeman Press, New York, 2nd ed. 1982). and in Copeland, Robert. *Analytical Methods for Proteins*, (American Chemical Society Short Courses 1994). both of which are wholly incorporated herein as prior art. Many of these enumerated optical and structural methods are rapid, cost-effective and accurate.

Experiments were performed using model systems to show the conformational changes involved in the transition from a predominately alpha-helix to a beta-rich form. The model systems chosen used readily available, nonneurotoxic polyamino acids such as polylysine and polyglutamine. The polyamino acids were chosen because of their availability and more importantly because they are safe to handle thus eliminating the need for special handling or donning cumbersome extra protective gear.

FIG. 3 shows a circular dichroism graph of experimentation with poly-L-lysine 20 micro Molar (μM) 52,000 molecular weight (MW) as a peptide probe. The resulting graphs show:

Sample 24 which was maintained at pH7, 25° C. resulting in a minimum at approximately 205 nanometers (nm) indicating random coil structure.

Sample 26 which was maintained at pH11, 50° C. resulting in a minimum at approximately 216 namometers (nm) indicating beta-sheet structure.

Sample 28 which was a 1:1 combination of samples maintained at pH7, 25° C. and at pH11, 50° C. resulting in a minimum at approximately 216 namometers (nm) indicating beta-sheet structure.

Sample 30 which was a 1:1 combination of samples maintained at pH7, 50° C. and at pH11, 50° C. resulting in a minimum at approximately 216 namometers (nm) indicating beta-sheet structure.

FIG. 4 shows an absorbance graph of experimentation with poly-L-lysine 70 mircomolar (μM) 52,000 molecular weight (MW) as a peptide probe. The resulting graphs show:

Sample 32 which was maintained at pH 11, 25° C. resulting in a plateau at approximately 0.12 indicating predominately alpha-helical structure.

Sample 34 which was maintained at pH7, 50° C. resulting in a a plateau at approximately 0.22 indicating random coil structure.

Sample 36 which was a 10:1 combination of samples maintained at pH7, 50° C. and at pH11, 50° C. resulting in a steeper incline from approximately 0.22 to 0.33 indicating an accelerated transition from random coil to beta-sheet structure.

Sample 38 which was a 10:1 combination of samples maintained at pH7, 25° C. and at pH11, 50° C. resulting in a gradual incline from approximately 0.22 to 0.26 indicating a transition from random coil to beta-sheet structure.

Figure 4:
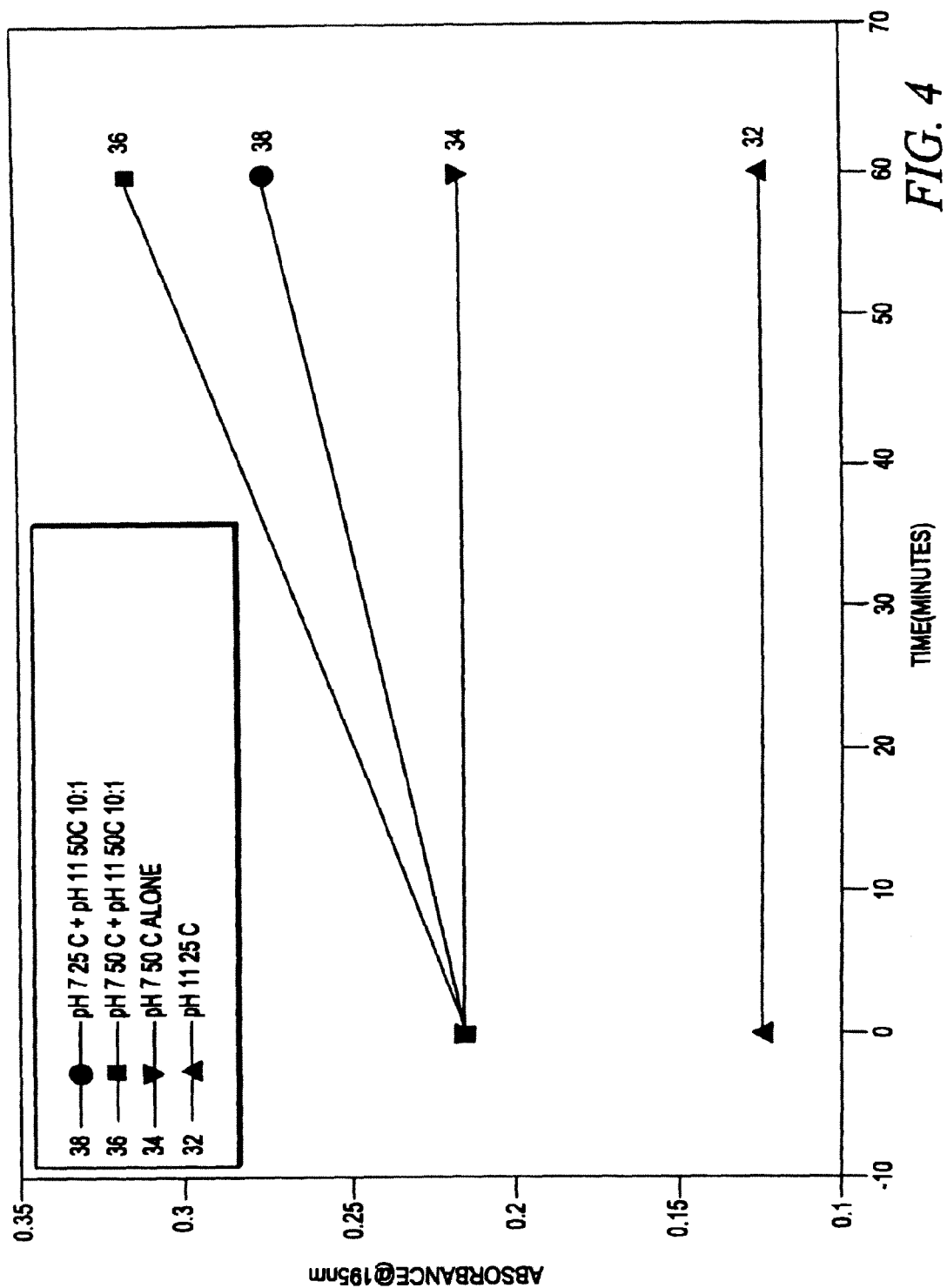

FIG. 4 shows general circular dichroism results of experimentation with poly-L-lysine at varying temperatures and pH indicating its potential for transitioning from random coil to beta-sheet under the varying environmental conditions. The results indicate that both temperature and pH play an important role in the transition.

The observations based on all of the modeling experimentation described above show that the addition of a relatively small amount of beta-sheet peptide to random coil sample can result in a shift towards a beta-rich conformation and such changes can be accelerated depending on the temperature and pH environment of the samples.

Figure 6:
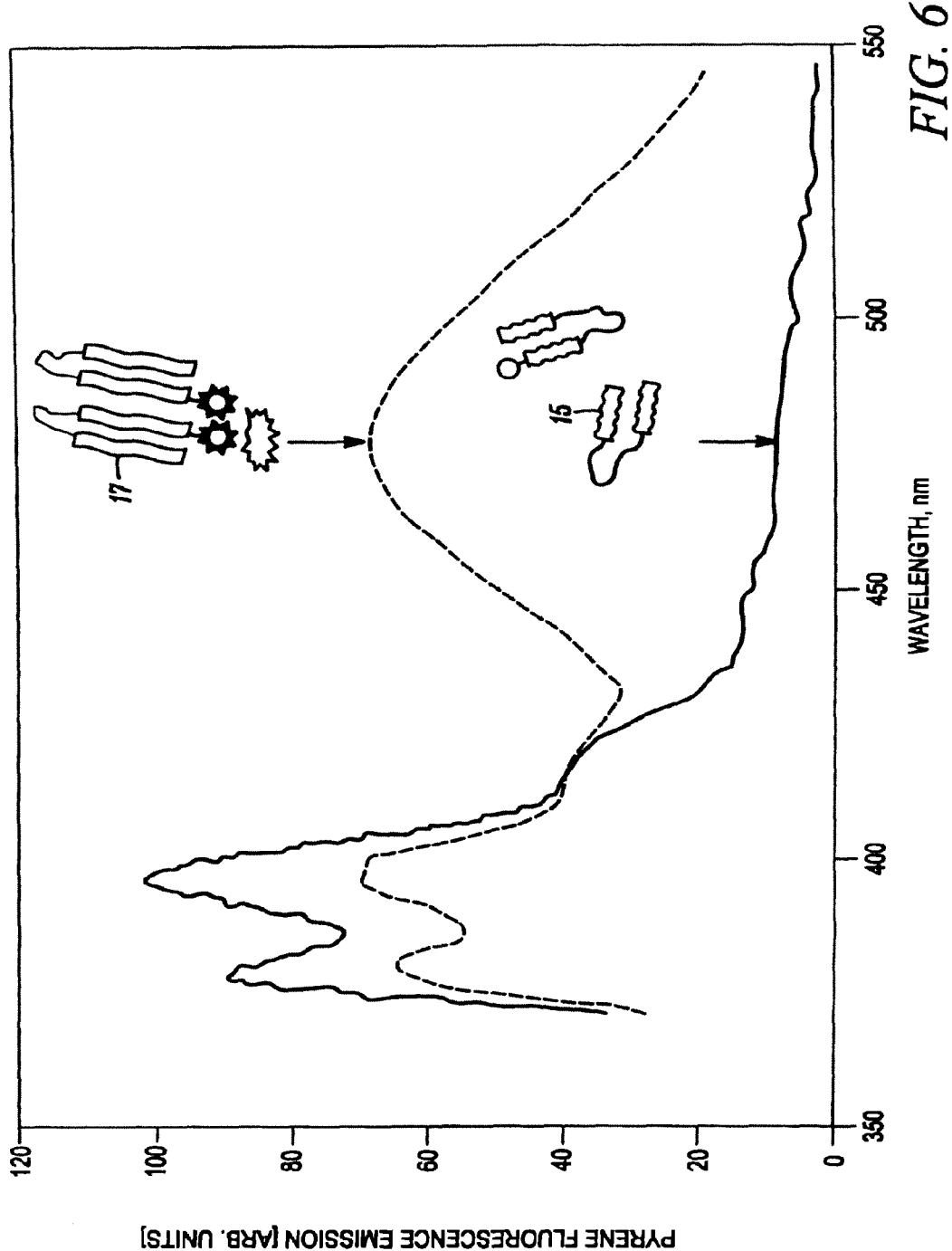
Figure 7:
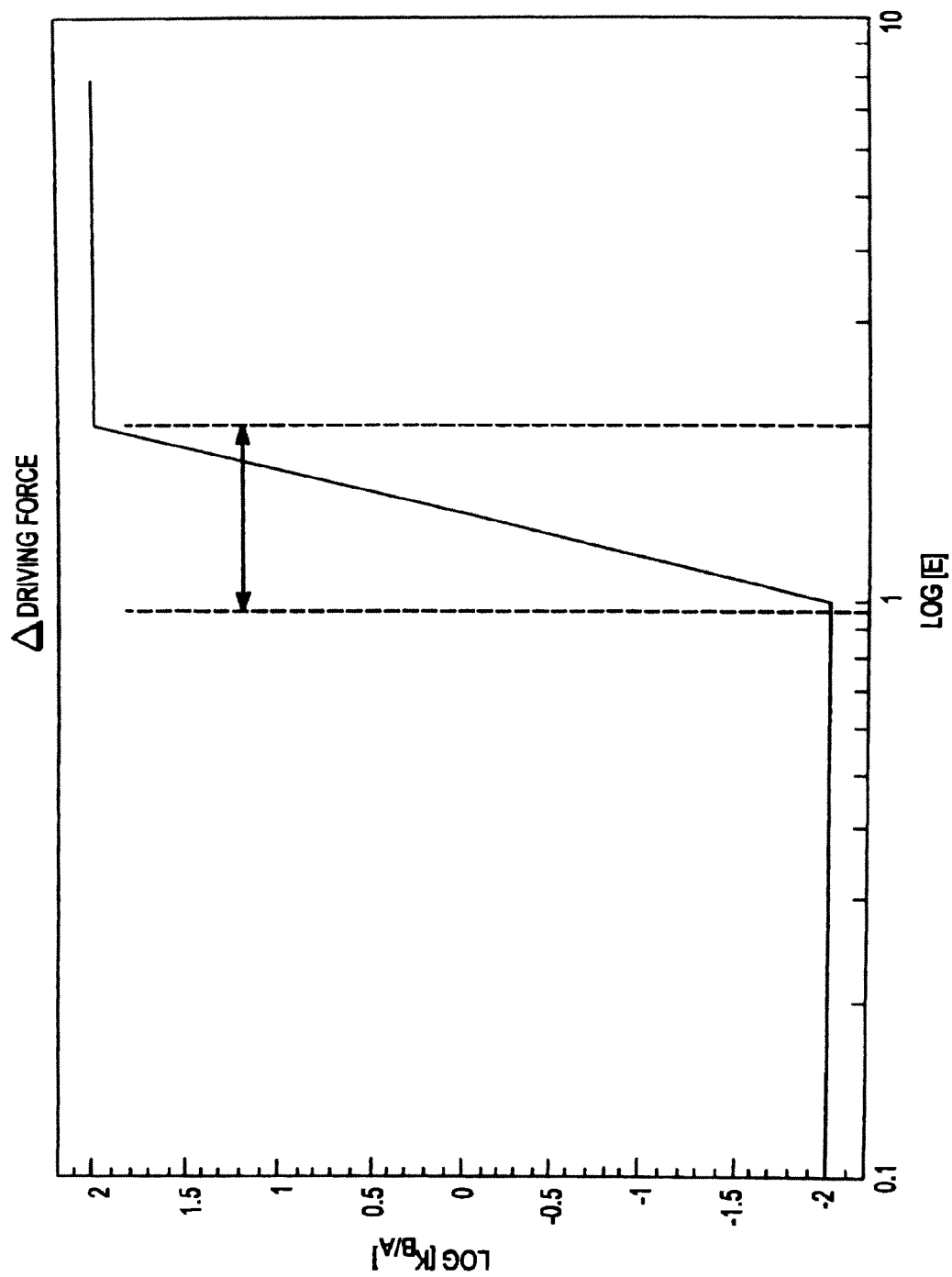
Figure 9:
Figure 8:
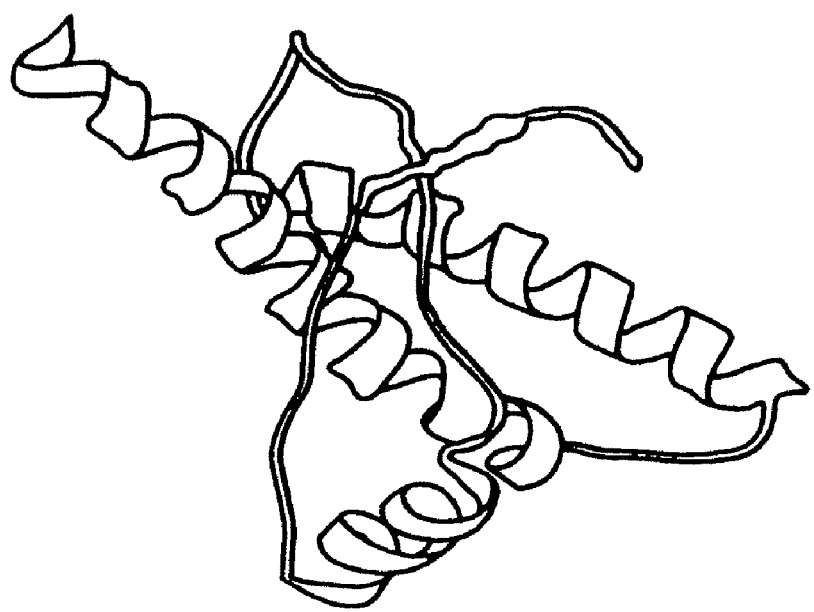

FIG. 6 shows experimentation results using pyrene as a fluorescent probe in proximal and distal locations in an alpha helical bundle structure undergoing conformational change. The pyrene excimer formation 42 is shown at 480 nm and the spectra for a predominately alpha-helical structure 40 is contrasted as well. Those skilled in the art would appreciate that other fluorescent probes such as FITC can also be used.

A primary objective of this invention also encompasses use of the catalytic propagation of conformational change to directly correlate the measures of abnormal prion presence with levels of infectivity. For this reason we favor implementation of the invention in a manner where there is no increase in resulting infectious products as a result of the propagation. This can be achieved by placing a "break" in the links between the chain of infection, transmission and propagation of the abnormal form. Such a "break" must occur at the transitional stage between the dimer and multimer forms of the aggregate. The physical formation of the multimer form can be blocked by simply impeding the step which leads to its formation. This may be done, preferably by using a large pendant probe or by a neutral "blocker" segment, bearing in mind that probes on linkers or "tethers" are more likely to encounter each other and thus result in amplifying the signal.

In a particularly preferred embodiment of the invention, the peptide probes 14 function in the manner described above. The peptide probes act as "nuclei"; wherein once the peptide probe 14 binds to a test sample 20, or a sample known to have beta-rich structure 12, it is converted to a peptide probe conformer 16 which has the capacity to act as a trigger to bind to another peptide probe 14 and continues to induce the same conformational change. Propagation of this reaction can then be controlled by the peptide sequence chosen for the peptide probe 14 and by the experimental conditions. Thus, in situations where infectious levels are low and there is a need to amplify any existing abnormal proteinaceous particles in an unknown sample 20, it is preferred that a peptide probe 14 capable of rapid and continuous propagation of the reaction be chosen with which to nucleate the unknown sample 20. On the other hand, in situations where it is desired to correlate detection of abnormally folded proteinaceous particles with levels of infectivity, it is preferred that peptide probe 14 chosen is one that is less likely to aggregate.

When more than one beta units come together, they act as nuclei to attract and stabilize other transient elements of secondary structure. See Stryer, Lubert. *Biochemistry*. W. H. Freeman Press. (3rd ed. NY 1988) p 35. In choosing the peptide probe 14 with which to nucleate this reaction there are several considerations to be made. Associations of peptide can be controlled by the thermodynamics of the solution in which they are in and by the presence of amorphous nuclei which self-associate, crystalline nuclei which readily aggregate, specific peptide sequences which may aggregate, but may do so under low concentrations which are difficult to measure by conventional means, or larger peptide sequences modeled after known beta-sheet structures or proteins such as a beta-rich prion protein.

To demonstrate this embodiment of the invention, two peptide sequences were synthesized to be used as peptide probes 14. The peptide sequences were modeled after known prion protein (PrP) sequences shown in FIG. 13. The sequences in FIG. 13 correspond to binding regions that are very similar among the species shown. FIG. 14 shows the peptide sequences of the two synthesized peptides. The 19-mer sequence referred to as Seq. Id. No. 19 is closely modeled after residues 104 through 122 of the human sequence. The 14-mer sequence referred to as Seq. Id. No. 14 is closely modeled after residues 109 through 122 of the human PrP sequence. The synthetic peptide probes 14 were also prepared with and without pyrene butyric acid as a fluorescence marker.

Many experiments were performed to study the properties of the synthetic peptides. Experiments were performed using analytical techniques common in the art such as absorbance, fluorescence under varying excitation and excitation of fluorescence. The peptides were studied at several concentrations ranging from 1 to 100 micro Molar (µM) and under varying buffer concentrations, pH, temperatures and ionic strengths.

Figure 15:
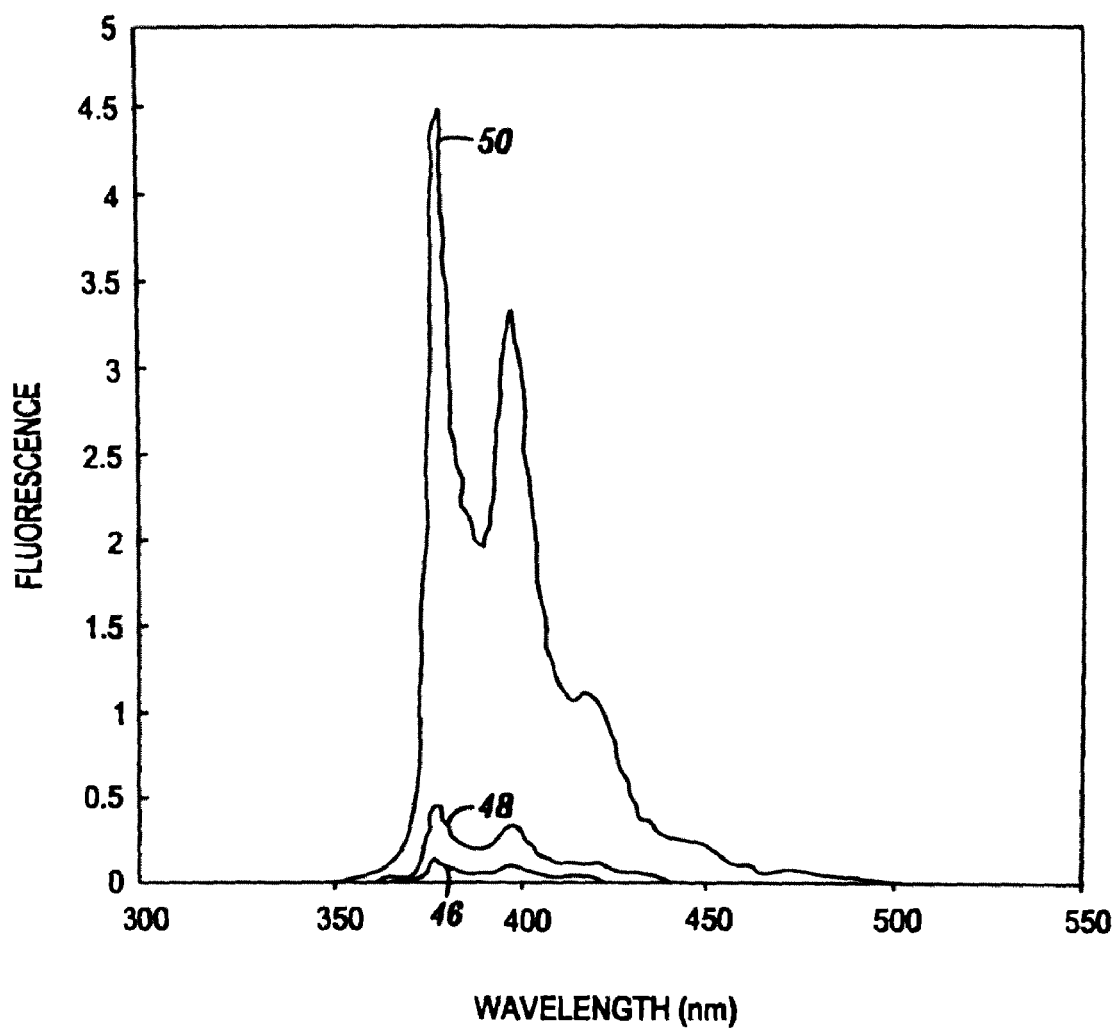

FIG. 15 shows a graph of fluorescence-spectra results at different peptide concentrations. The data were collected over times ranging form one hour to one week with no experimental changes observed after twenty-four hours. The resulting graphs show:

Sample 46 which was at a concentration of 5 µM with a relative fluorescence peak at approximately 0.1.

Sample 48 which was at a concentration of 10 µM with a relative fluorescence peak at approximately 0.4.

Sample 50 which was at a concentration of 150 µM with a relative fluorescence peak at approximately 4.7.

Note: data were also collected for Sample 52 at a high concentration of 800 µM, but is not shown in the figure.

Figure 16:
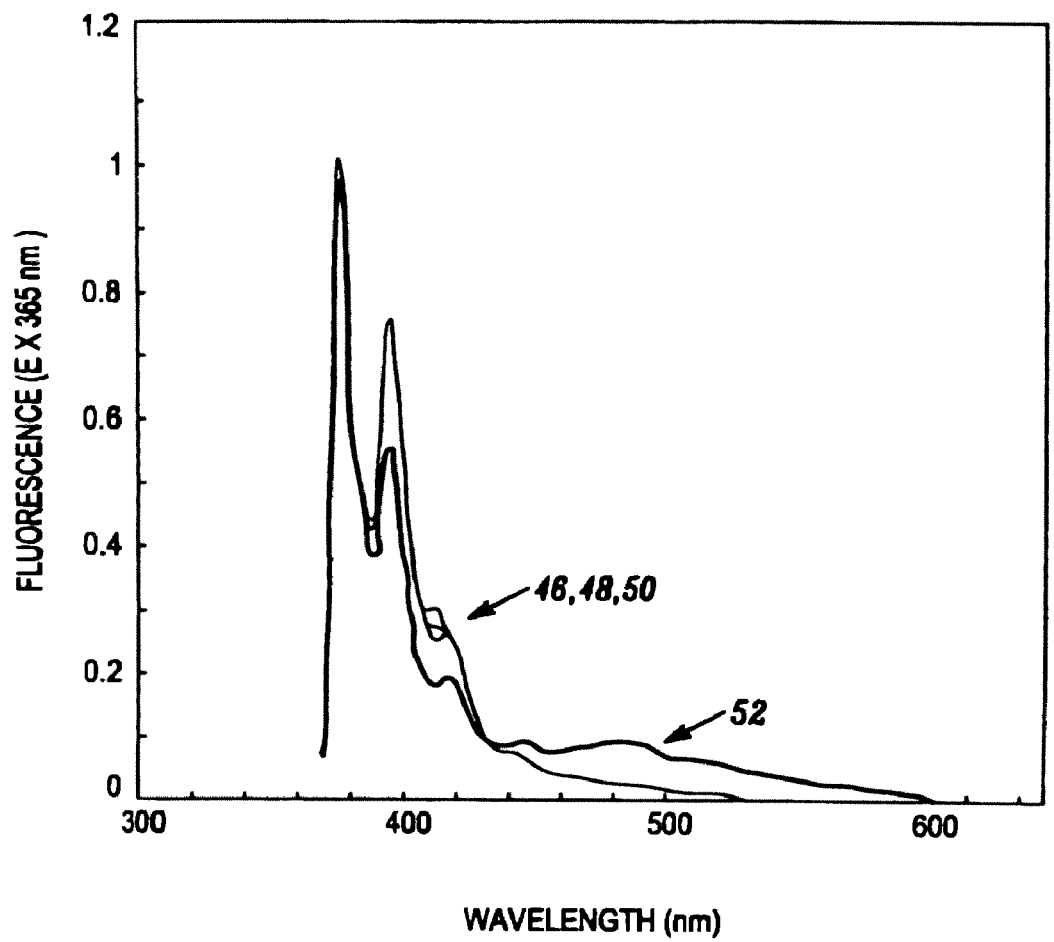

FIG. 16 shows a graph of the fluorescence spectra for samples 46 through 52 normalized to the intensity at 378 nm for the initial scan. It was observed that the spectrum for Sample 52 which contained the highest peptide concentration was markedly different leading to the conclusion that there is excimer emission with a maximum at approximately 460 nm.

Figure 17:
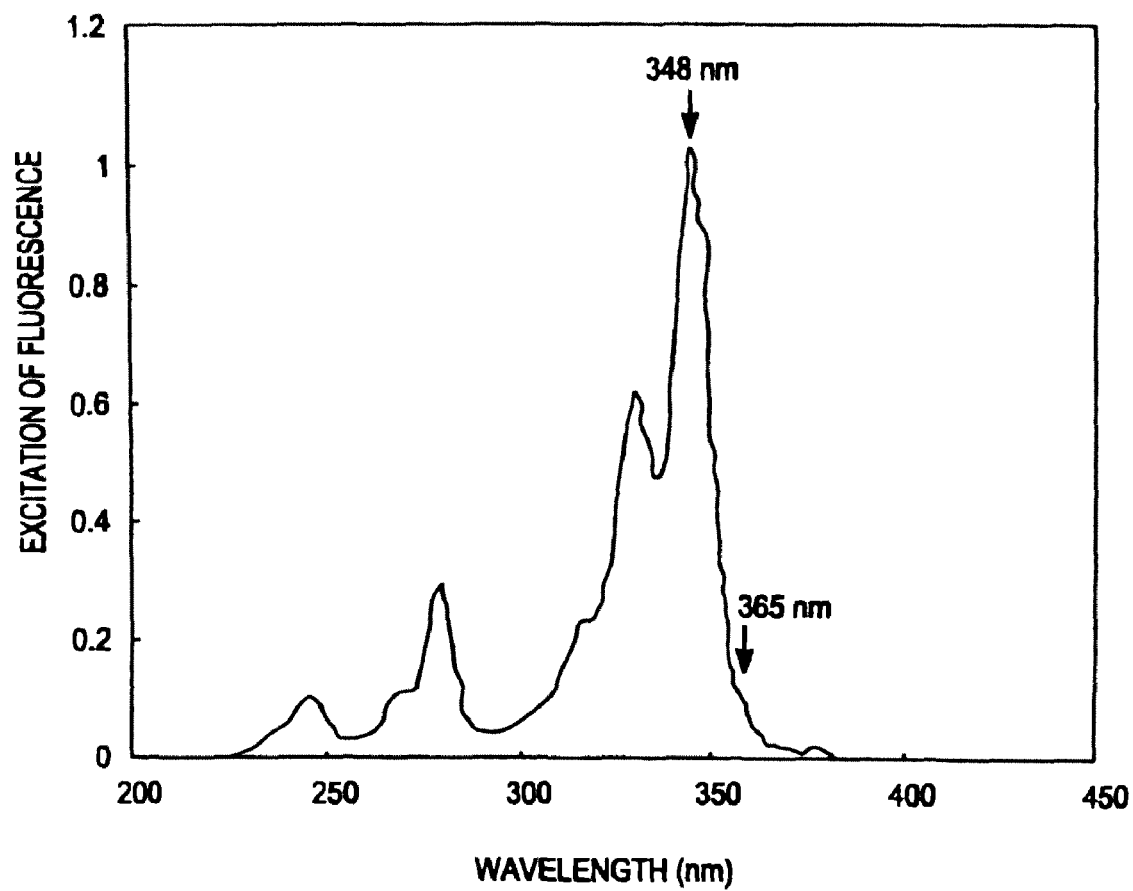
Figure 18:
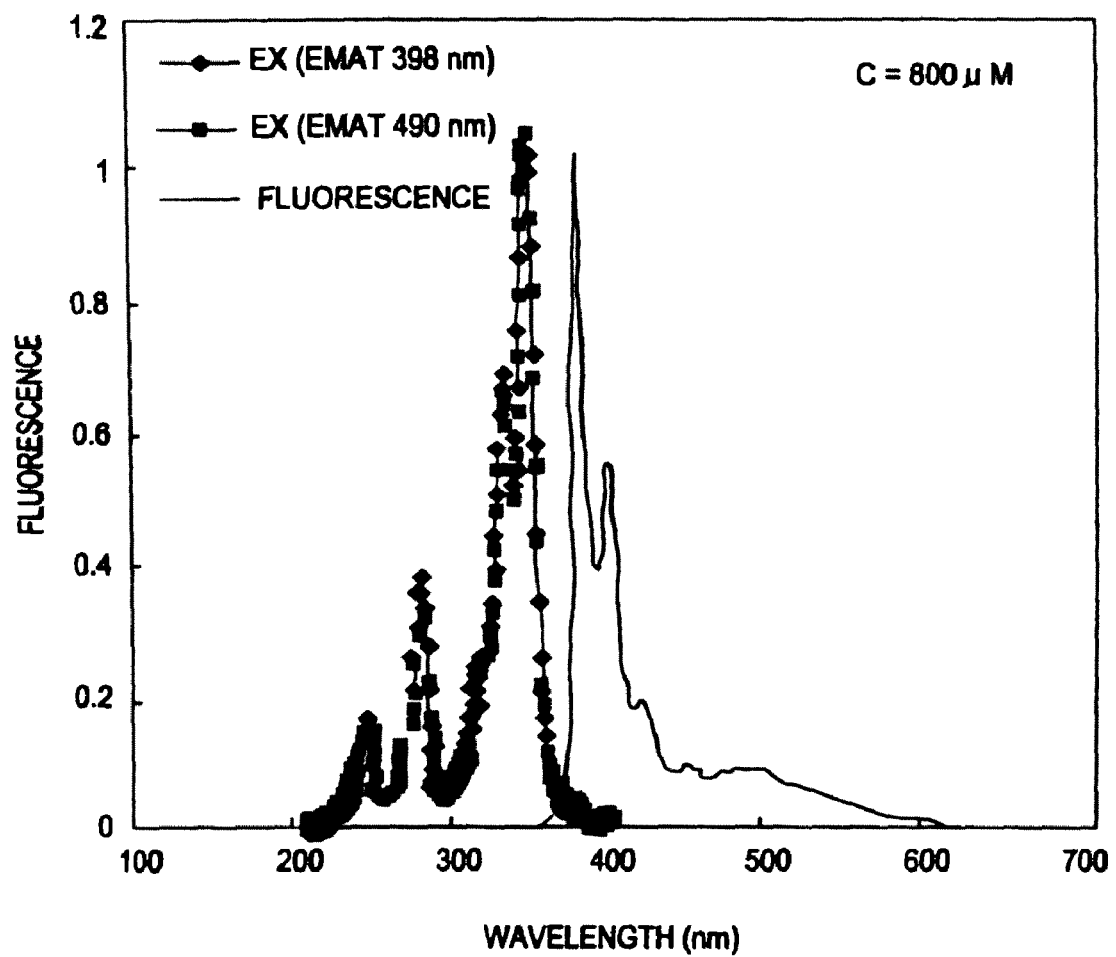

FIG. 17 is a graph of experimental results showing pyrene's excitation of fluorescence. The experiments were performed with excitation wavelengths at 365 nm to observe excimer emission at approximately 460 nm. The excitation at 348 nm, however, increases the fluorescence signal by over a hundred times with no other modifications or signal amplification. To confirm that the pyrene conjugate was responsible for both the major 398 nm emission as well as the one at approximately 460 nm, the excitation spectra for fluorescence at 398 nm and at approximately 460 nm were recorded and are shown in FIG. 18. Both the excitation spectra are nearly identical with a 365 nm maximum confirming that emission at approximately 460 nm is associated with the formation of excimers by two pyrene groups as in the following.

$$Pyr^*Pyr = (Pyr\_Pyr)^*$$

where Pyr is a pyrene molecule and Pyr* is a pyrene in its excited form; the (pyr_Pyr)* represents the formation of excited dimer. More general information on excimers can be found in Freifelder, David. *Physical Biochemistry: Applications to Biochemistry and Molecular Biology*, (W. H. Freeman Press, New York, 2nd ed. 1982), at 559.

Figure 19:
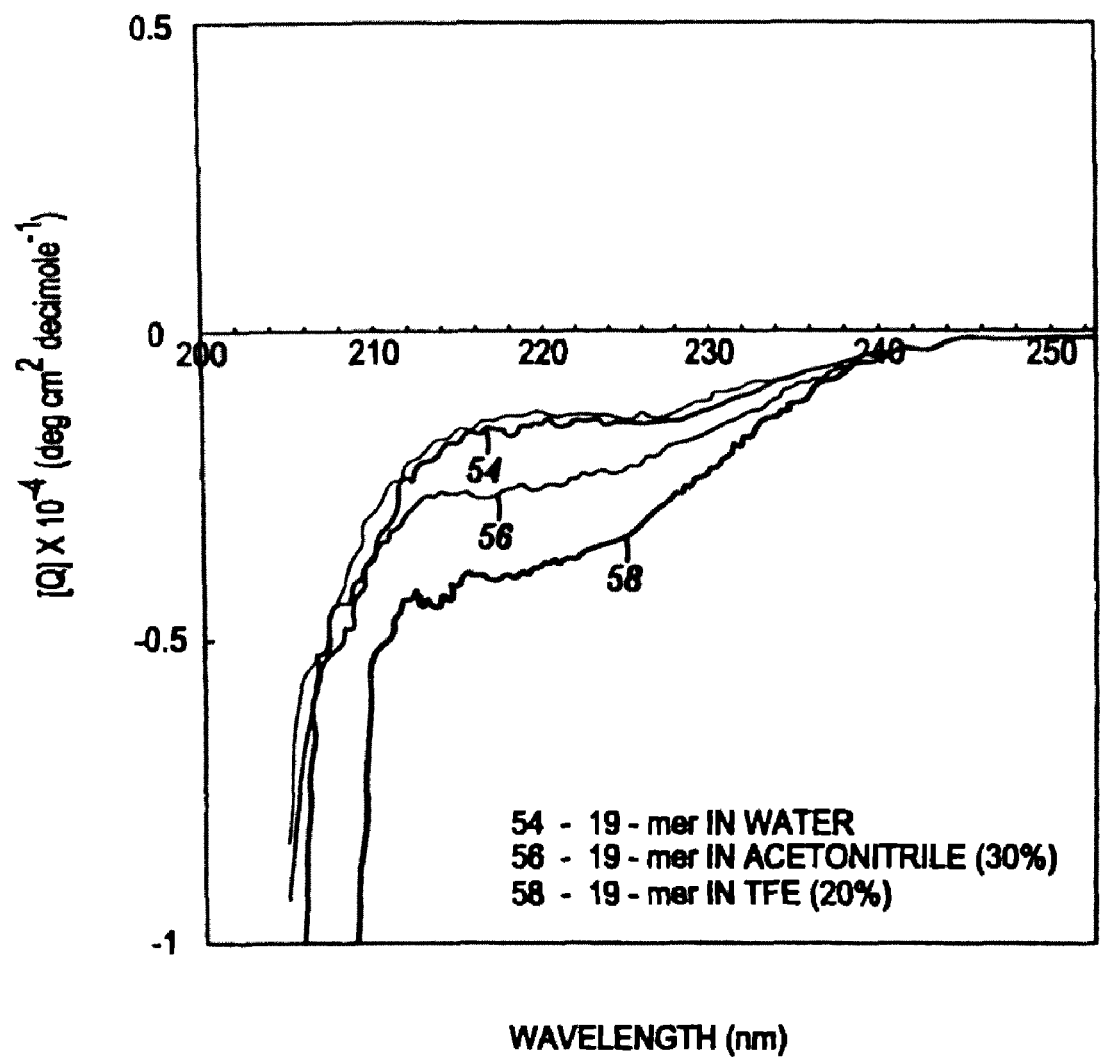
Figure 20:
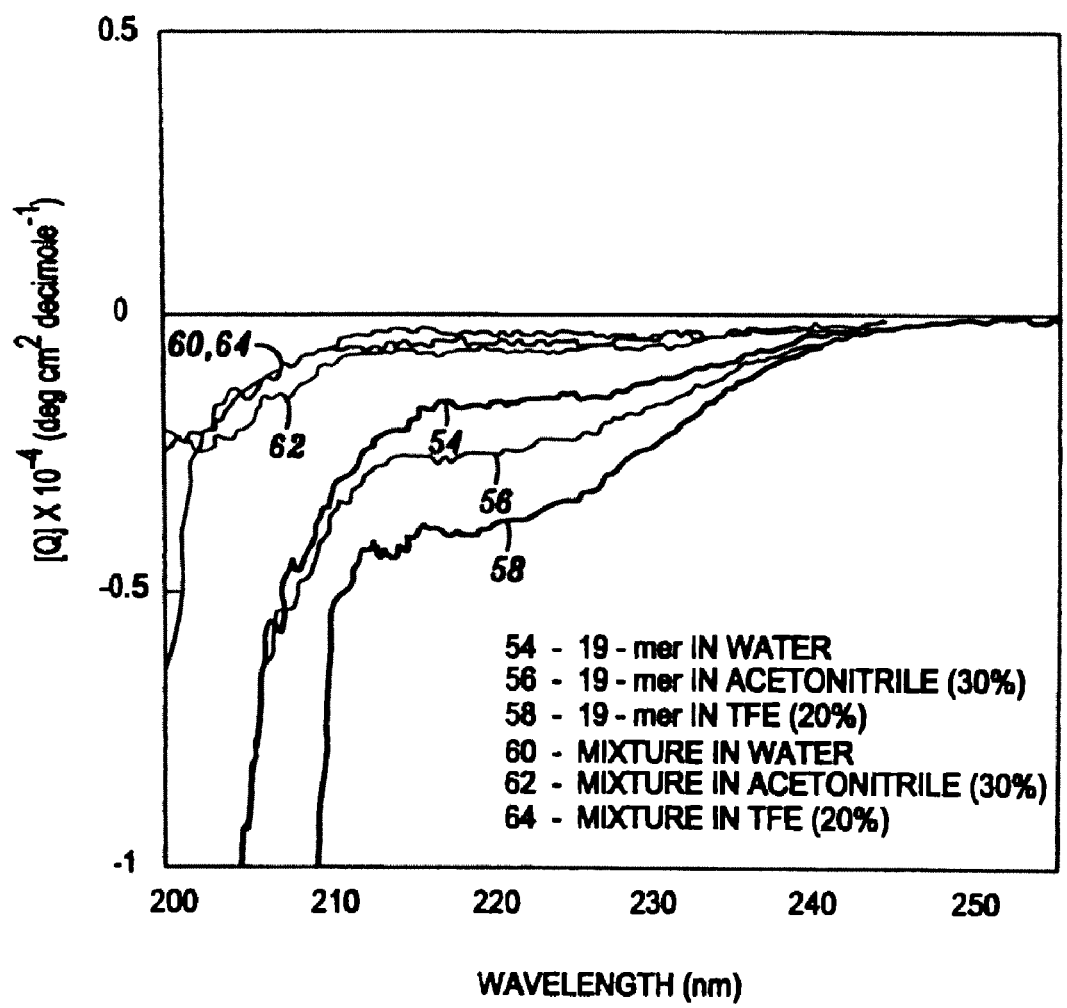

Experiments were also performed to study the stability of the peptides. FIG. 19 shows experimental data obtained from circular dichroism (CD) analysis of the 19-mer under different condition. The CD spectra were recorded for a number of peptide concentrations ranging from 20 to 100 mM. The results show that the 19-mer is largely coiled and exhibits high thermodynamic stability under the experimental conditions tested such as varying pH, ionic strength and temperature. As expected, the addition of organics such as acetonitrile and trifluoroethylene (TFE) encourage the formation of the secondary structure. FIG. 20 shows both the previous results and the results of a similar experiment in which the 19-mer was mixed with its shorter analog, the 14-mer. In this experiment, the 19-mer and 14-mer were combined 100:1 for one hour and assembled under dilute conditions in the micro molar range. Sample curves 60 through 64 which correspond to the mixture showed that the mixture of the oligomers significantly differed from the CD spectra of sample curves 52 through 58 which represent the 19-mer alone, indicating strong interactions between the mixed molecules. As a result, the 14-mer triggers conformational changes in a peptide probe 14 made of the 19-mer.

Figure 21B:
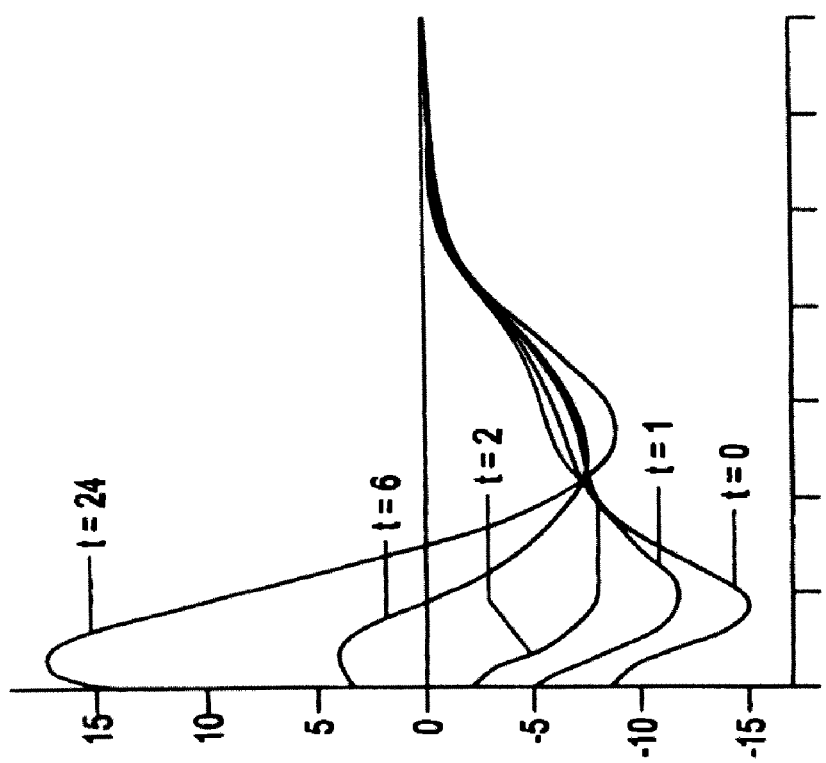
Figure 21A:
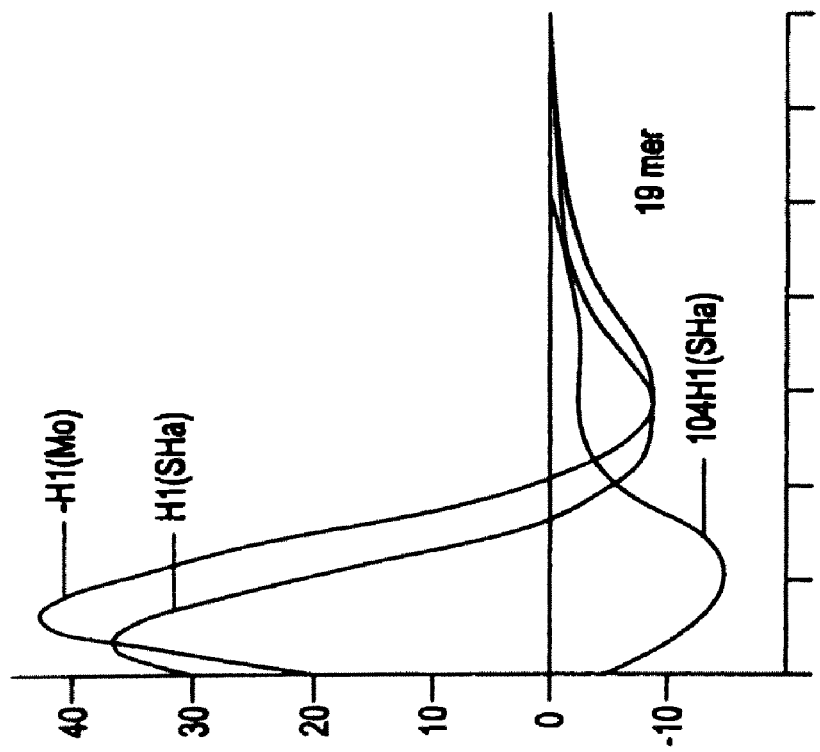

In a paper published by Prusiner, et al., CD data show that the Seq. Id. No. 19, 19-mer exhibits coil-like conformation, whereas the Seq. Id. No. 14, 14-mer is largely beta-sheet as shown in FIG. 21*a* for a 3 mM concentration sample from the paper. The 19-mer, however, can be transformed from its coil-like conformation to a beta-sheet conformation through interaction with a very small fraction of the 14-mer as shown in FIG. 21*b* which was tracked over a twenty four hour time period. See Prusiner, et al. *Prion protein peptides induce alph-helix to beta-sheet conformational transitions*. Biochemistry. 34:4186-92 (1995).

Figure 22:
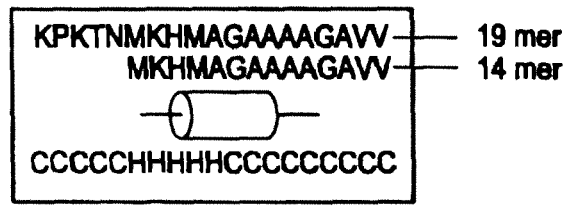

FIG. 22 shows a conceptual figure of the secondary structure of the two synthetic peptides (where C=coil and H=helix) based on the application of various secondary structure algorithms to the sequences of both of the synthetic peptides. The resulting projection, however, does not entirely agree with the CD results. Based on the CD results, the conformations of both synthetic peptides are clearly concentration dependent. Moreover, while the 19-mer exhibits largely a coil conformation that is fairly stable under a wide variety of the experimental conditions tested, the 14-mer exhibits a transition from coil or hairpin to beta-sheet structure depending on its concentration.

Figure 23:
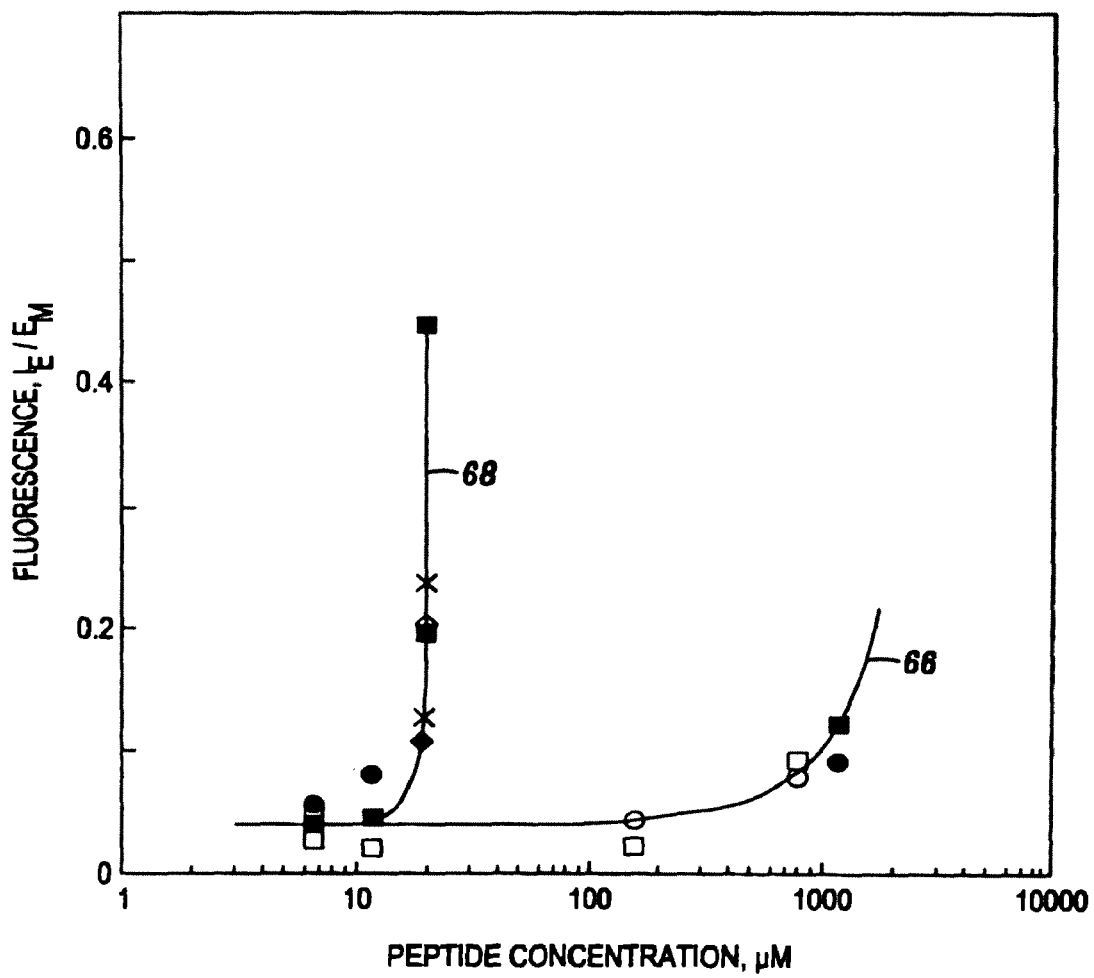

More experiments were performed to determine if the 19-mer could self-associate. FIG. 23 shows a graph of fluorescence results showing that the 19-mer could self-associate with increasing concentration as shown in Sample curve 66 and at low concentrations with pH modifications to give a net neutral charge while using potassium chloride (KCl) to screen the charge as shown in Sample curve 68. The 19-mer can also self-associate at low concentrations with the introduction of some type of nucleating agent, as discussed earlier. Thus, the conditions for self-association can be optimized to adapt to a desired type of detection.

Figure 24:
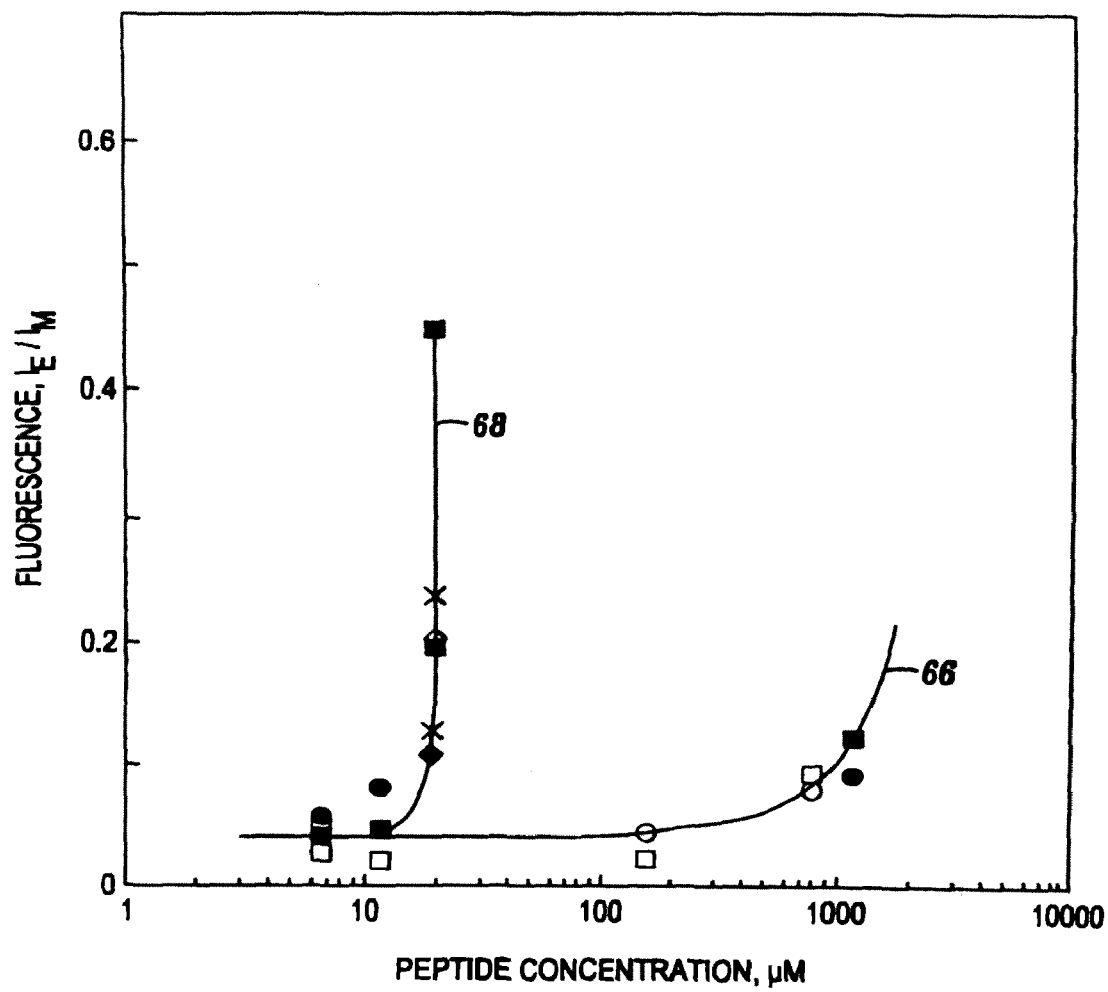

The same samples; Sample curve 66 containing 0.1 M TRIS buffer at pH 6 to 9 and Sample curve 68 containing 0.1 M TRIS buffer at pH 10 to 11 in the presence of KCl at 100 to 500 mM, are shown again in FIG. 24 to reflect the efficiency of excimer formation under low concentrations. The ratio of the fluorescence intensities as measured at 378 nm ($I_M$) and at 460 nm ($I_E$) was chosen to monitor the self-association as a function of the peptide concentration at 25° C. It was also shown that screening of the electro-static interactions (pI=10) encouraged self-association at extremely low concentrations on the order of less than 10 micro Molar.

Figure 25:
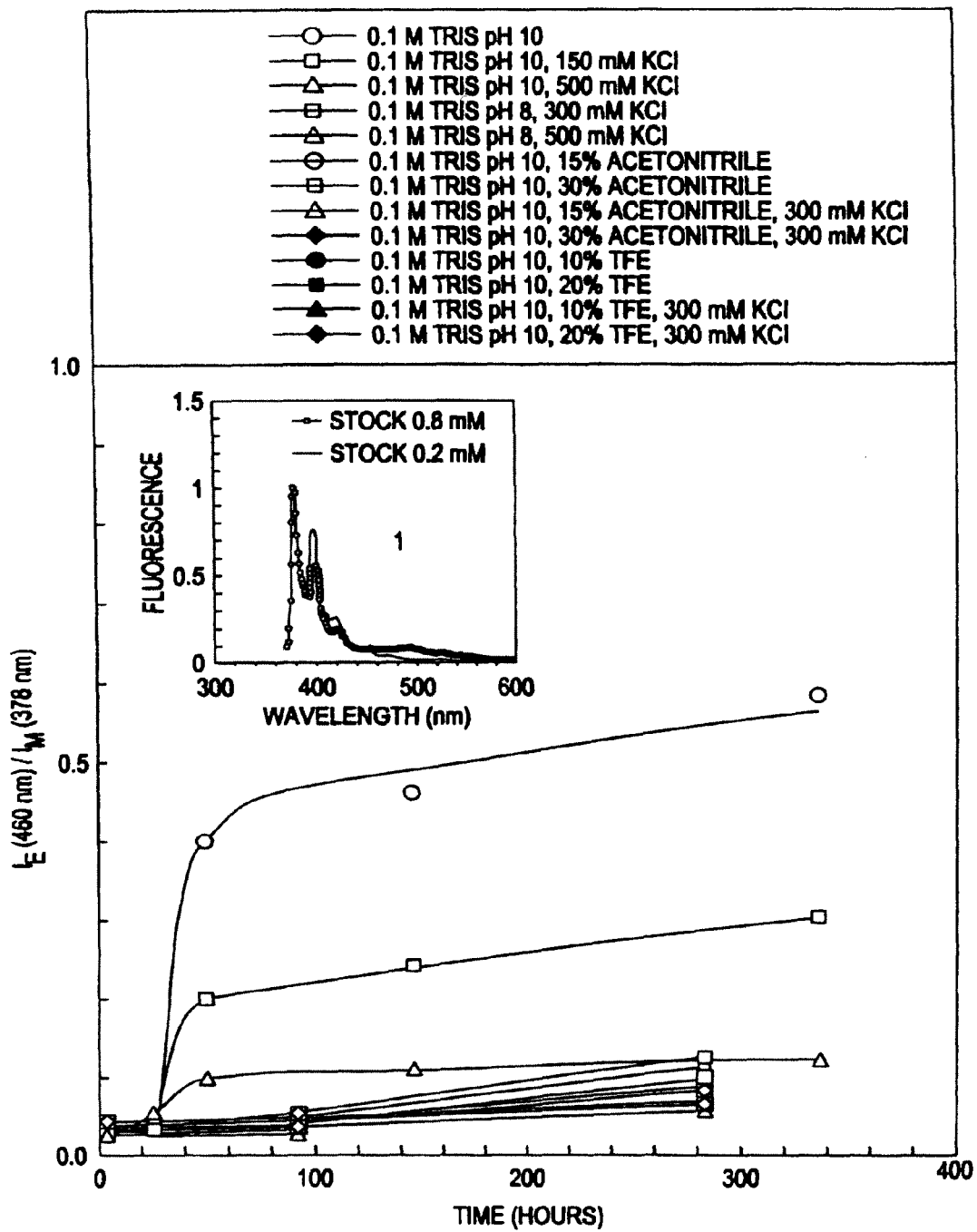

In order to further study the effect of nuclei on the self-association of the 19-mer, more fluorescence measurements were taken of 19-mer in solution nucleating with small amounts of already self-associated 19-mer units. The sample solutions range from concentrations of 200 to 800 micro Molar and are described in FIG. 25. The kinetics of association in dilute solutions of 20 micro Molar were also monitored.

Figure 26A:
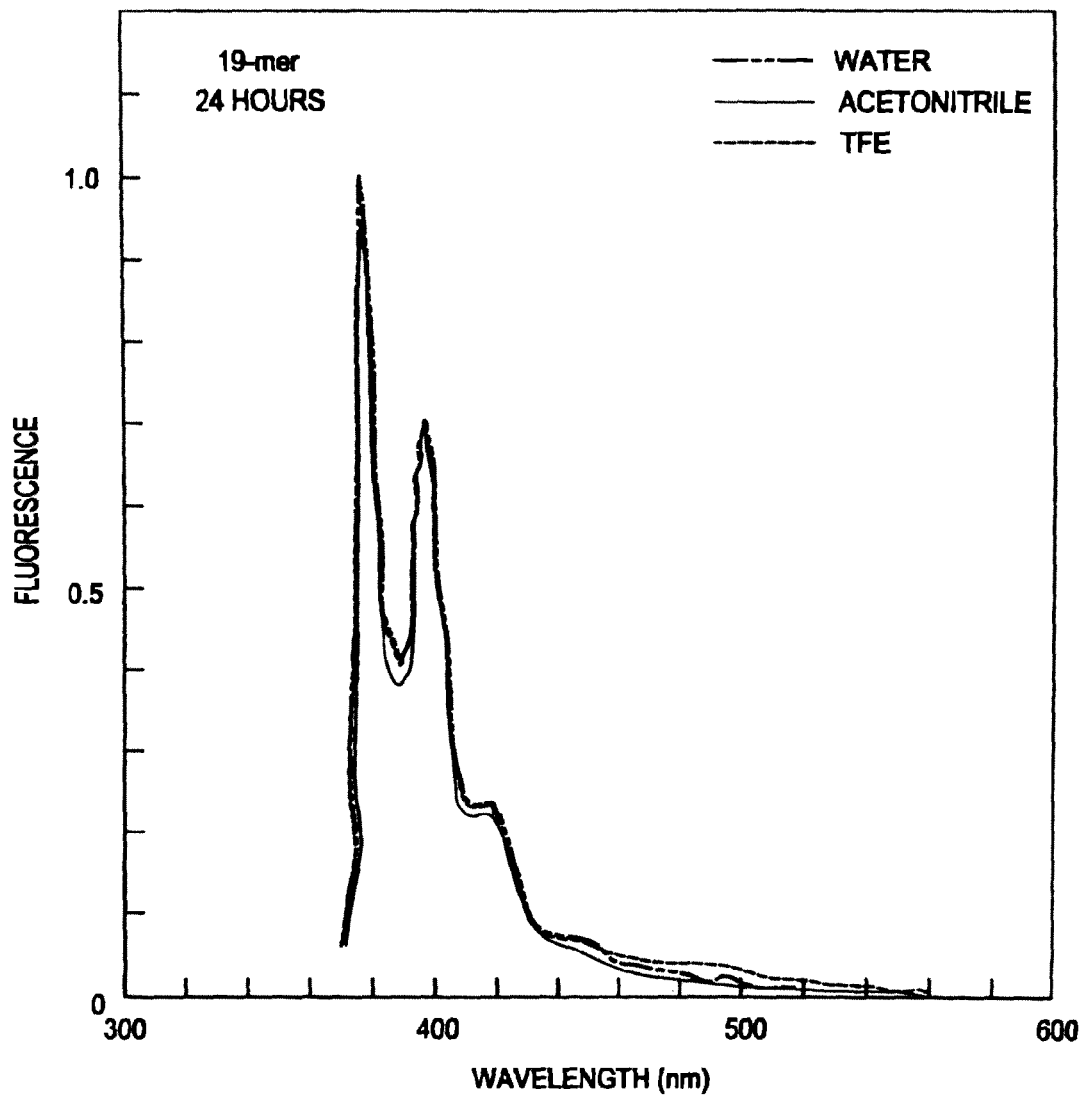
Figure 26B:
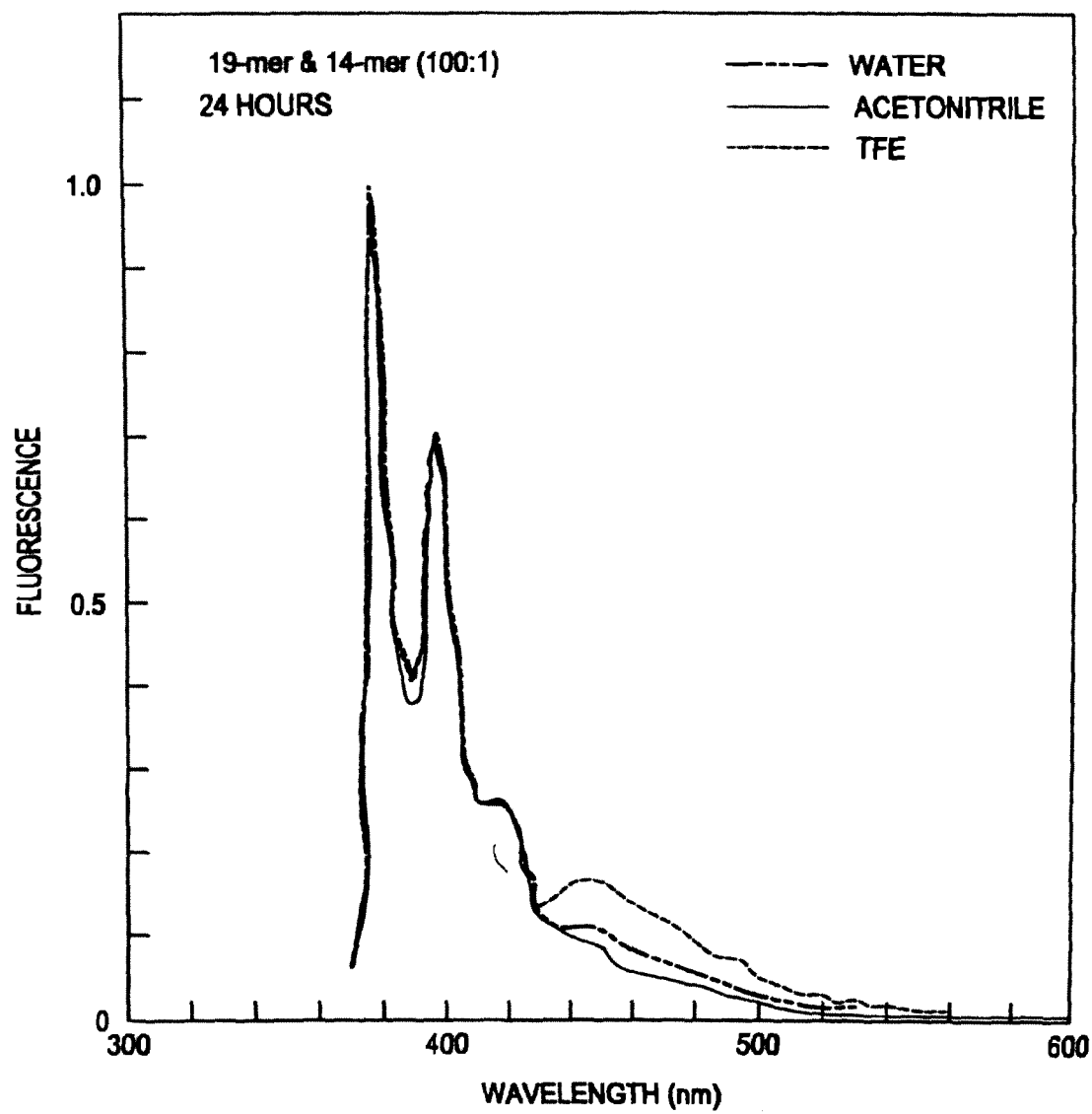

FIG. 26*a* shows more fluorescence data of the 19-mer in water 70, acetonitrile 72 and TFE 74 after twenty-four hours. FIG. 26*b* shows the experimental results for a 100:1 combination of the 19-mer and 14-mer in water 76, acetonitrile 78 and TFE 80 after twenty-four hours. In both of the graphs in FIG. 26 peptide association was monitored by the appearance of excimer emission at approximately 460 nm.

Figures 27A, 27B:
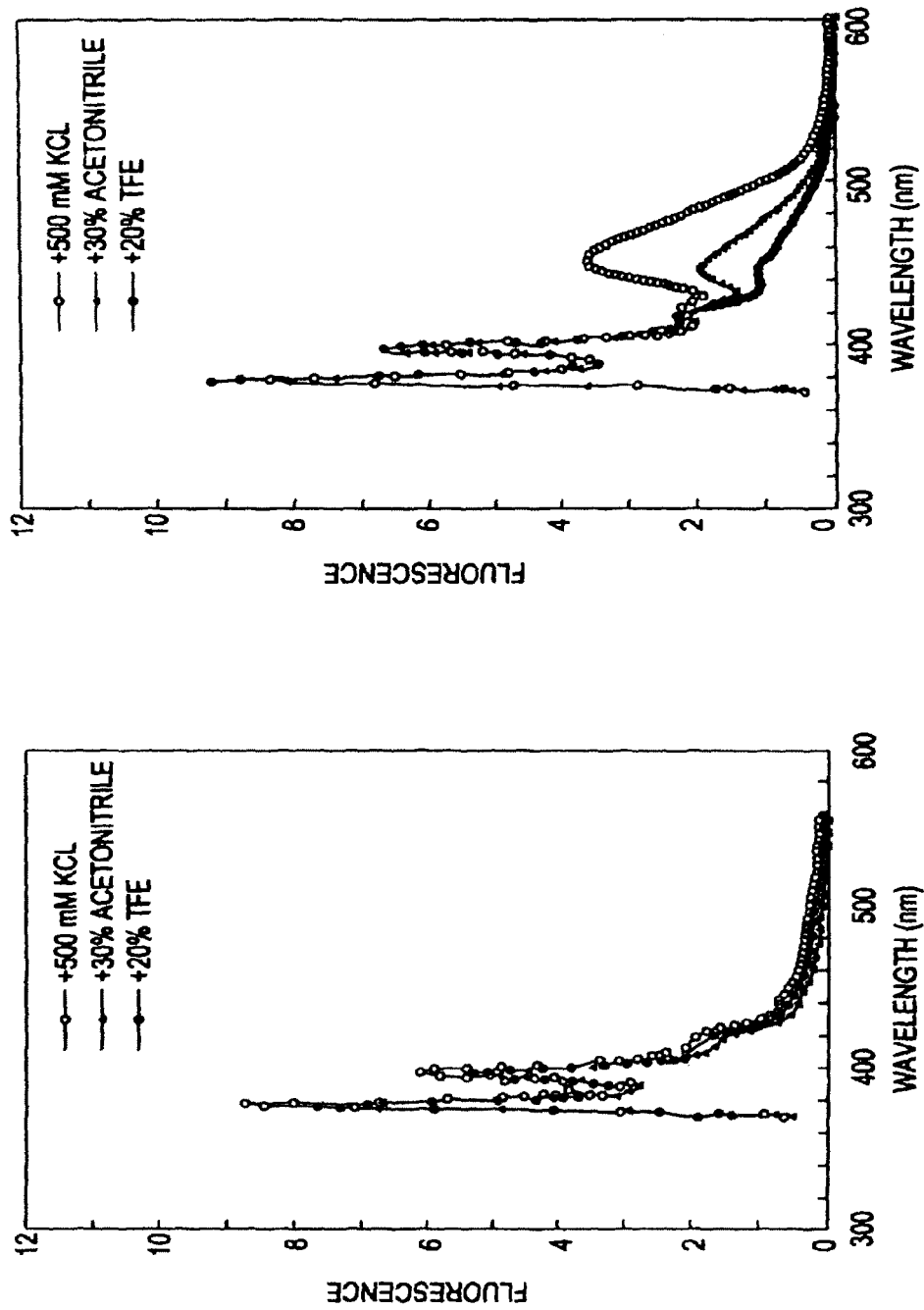
Figure 27D:
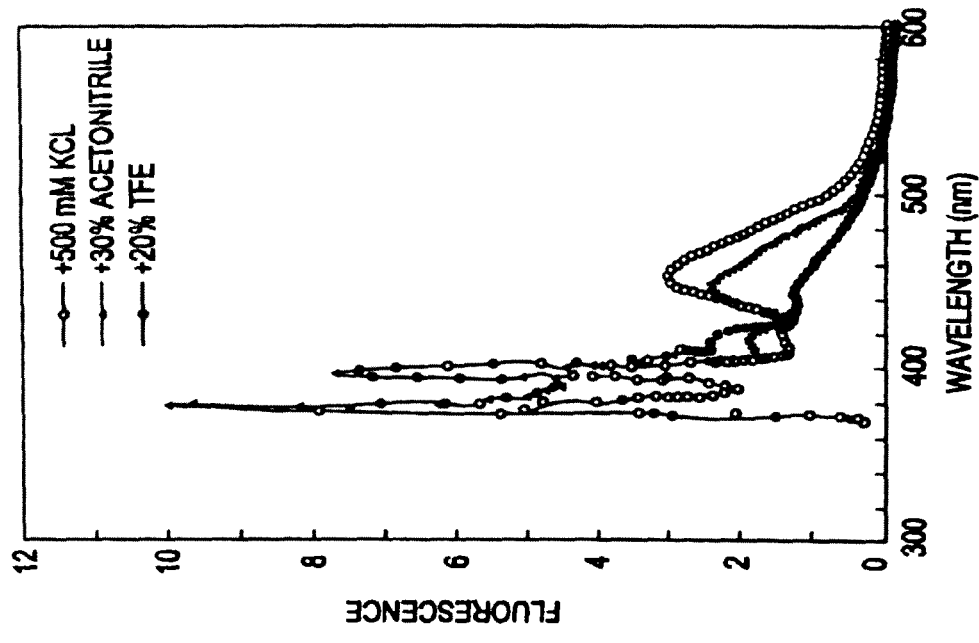
Figure 27C:
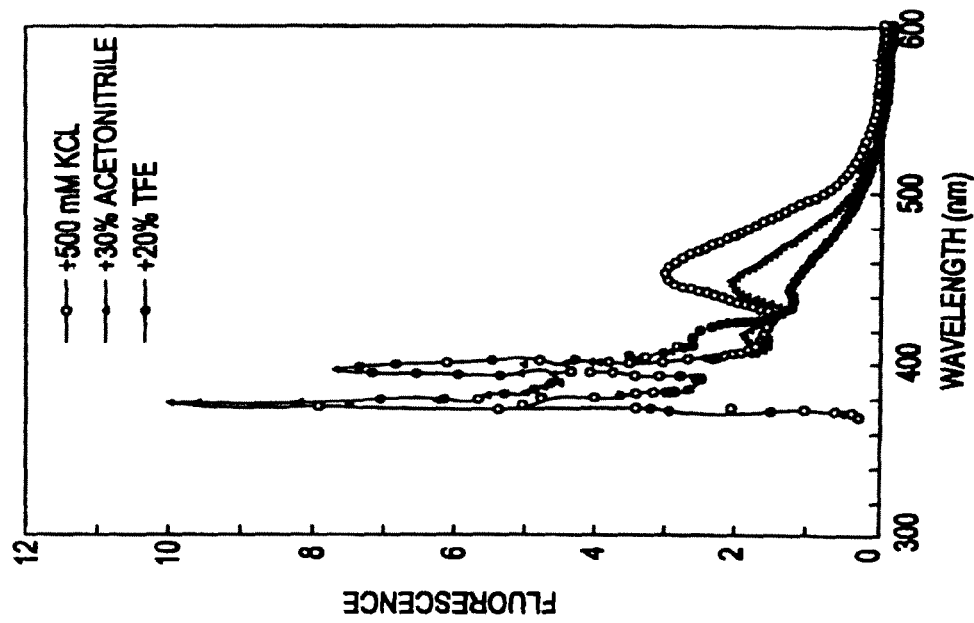

FIGS. 27 *a, b, c*, and *d* show four fluorescence data graphs taken at 24, 48, 144 and 336 hours, respectively. The measurements were taken to determine the effect of pH, temperature, ionic strength, and organic additives on the kinetics of the peptide associations studied for the 19-mer model peptide. The fluorescence intensities as measured at 378 nm for monomeric units and 460 nm for associations were used to characterize the $I_E/I_M$ ratio or self-association of the peptide.

Figure 28B:
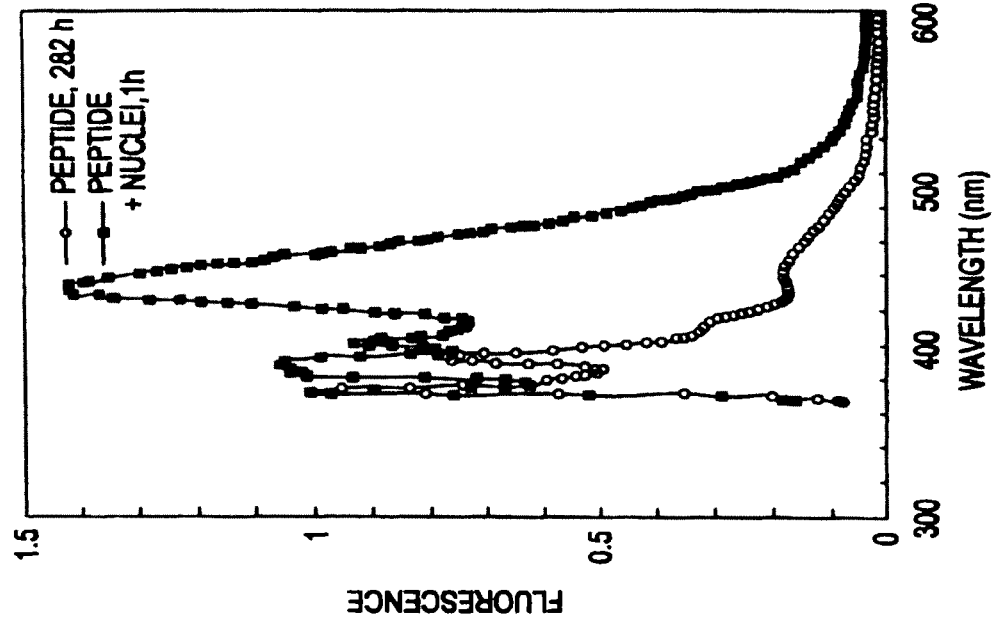
Figure 28A:
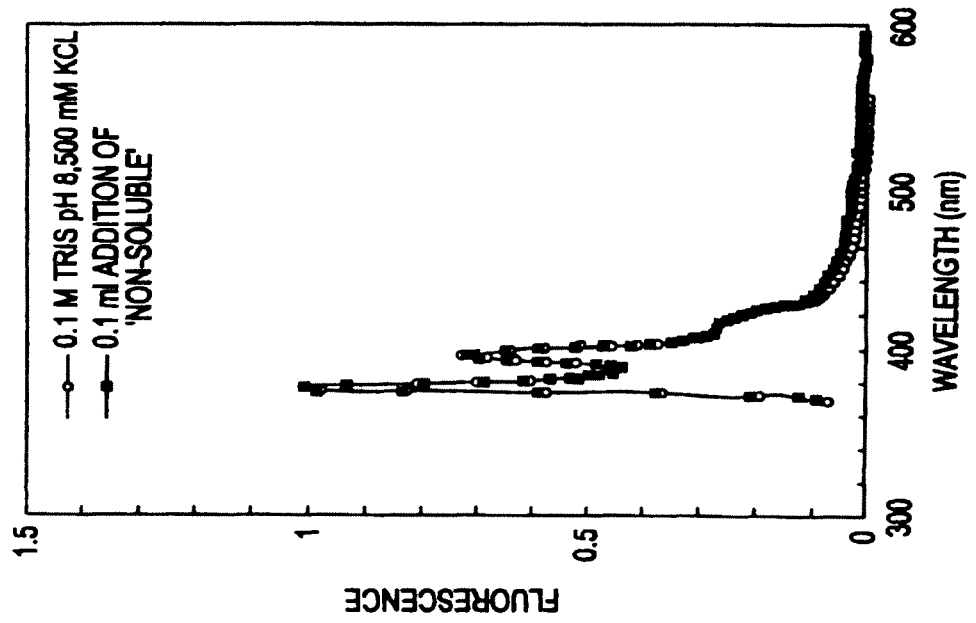

Additional fluorescence results are shown in FIG. 28 where an insoluble fraction of the peptide was extracted and dissolved in organic solvent containing methanol/ethanol/dimethylformamide and then analyzed. Fluorescence detection results of the "insoluble" portion show high levels of peptide association wherein the $I_E/I_M$ ratio equals 2. A small aliquot of "insoluble" portion was added to nucleate 20 micro Molar 19-mer peptide solutions which were then analyzed and are reported in the same graph. The results show that the presence of the nucleating fraction significantly increased the efficiency of the peptide association and this can be seen more dramatically in FIG. 28*b* at 150 hours.

The observations of these experiments led to some of the following conclusions.

Fluorescence of pyrene, which is covalently attached to the peptide probe 14 in preferred embodiments, allows monitoring of peptide self-association in this model system. It can also be used as an index of conformational change and especially since at low concentrations, the peptide association is difficult to measure using nonoptical techniques.

The fluorescence data shows that self-association of the Seq. Id. No. 19, 19-mer, can be promoted by adjusting ionic strength or pH.

The fluorescence data also shows that the kinetics of the conformational changes can be modulated by controlling solvent parameters and the peptide probe sequence.

The kinetics of the self-assembly or association process can be controlled or regulated by the addition of or by preexisting nucleating associated forms. This strongly supports the conclusions that the conformational transitions of the 19-mer can be autocatalytic.

In a particularly preferred embodiment, the peptide probes 14 can be used to detect proteinaceous particles such as in prion-like structures exhibiting coil to beta-sheet transition. According to Prusiner, et al. *Prion protein peptides induce alpha-helix to beta-sheet conformational transitions*. Biochemsitry. 34:4186-92 (1995). As a result, synthetic peptide probes such as the Seq. Id. No. 19, 19-mer should be conformationally sensitive to the presence of prion-like substances that undergo this conformational shift. Moreover, because an intrinsic optical reporter, such as pyrene can be added to the peptide probe, this embodiment of the invention has the added advantage of being able to detect such prion-like substances in test samples 20 such as blood, lymph, CSF and even tissues other than brain homogenate that typically contain very low levels of abnormal prion substances that are otherwise too difficult to detect. The intrinsic optical reporter allows optical (fluorescence) measurements to be taken of the peptide probe associates that form upon interaction with nucleating samples such as an abnormal prion.

In another particularly preferred embodiment of the invention, the peptide probes 14 are synthesized based on the structure of a dendrimer; dendrimers being synthesized three-dimensional highly branched macromolecules. The advantages of using a dendrimer probe 15 are multifold. Dendrimers should increase the speed of the assay kinetics thereby relaying quicker test results. This can be especially advantageous in assembly line applications of the invention where products or specimens in mass quantities can be quickly tested for the presence of abnormal proteinaceous particles. This embodiment is also extremely beneficial in applications where quick decisions must be based on the detection results. This embodiment is also advantageous for use in these applications as well as others since the highly branched structure of the dendrimer prevents amplification of abnormal proteinaceous particles or aggregates. By preventing such amplification of the abnormal particles, it becomes very simple to correlate the detection results with the level of abnormal aggregates existing in a test sample 20. Furthermore, it is also safe to handle since the synthetic probe itself is nonneurotoxic and amplifies signal without amplification of any highly infectious particles that may be preexisting in a test sample 20. Thus, it eliminates the need for extra precautions or sterilization in many of the steps of the assay method.

Figure 29:
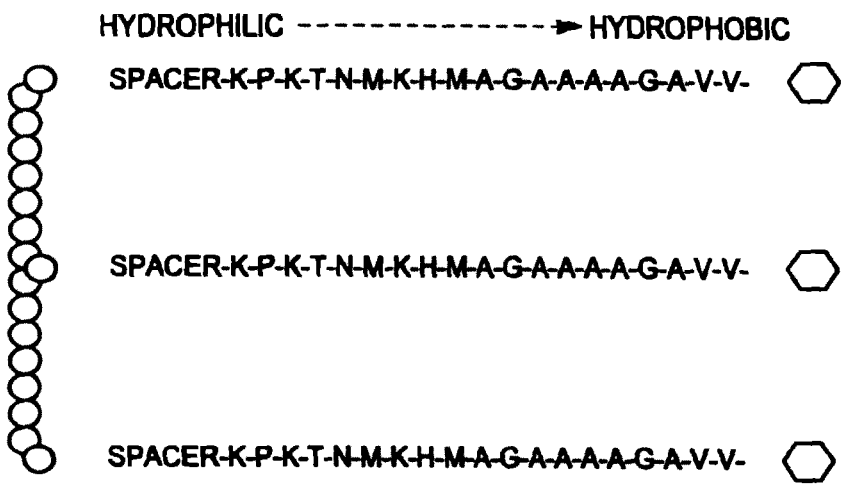

A generalized dendrimer 15 structure is shown in FIG. 29 and is referred to as Seq. Id. No. 20. In a particularly preferred embodiment of the invention, a specific dendrimer structure was designed and synthesized, referred to as Seq. Id. No. 22 and is shown in FIG. 30.

Figure 30A:
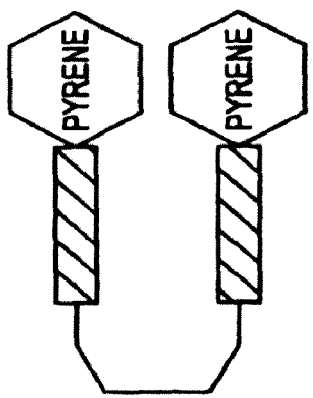
Figure 30B:
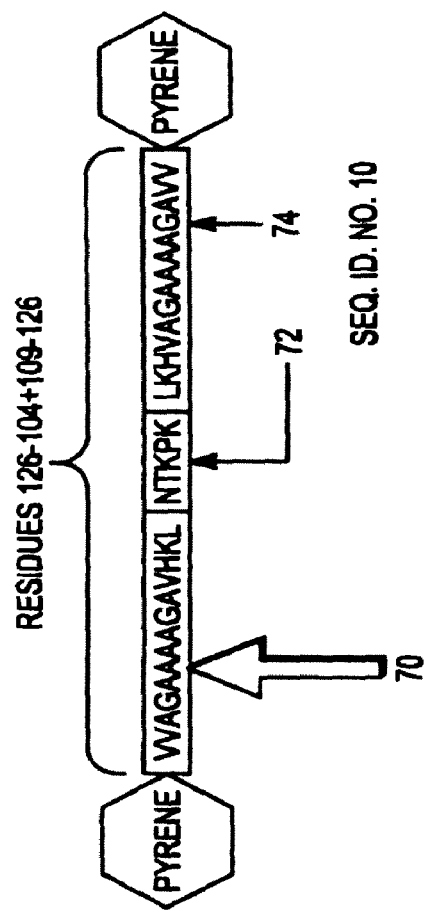

In FIG. 30, the specific dendrimer structure is basically a loop-turn-loop structure as illustrated by FIG. 30*a*. In FIG. 30*b*, it is shown that the sequence is modeled after the human PrP sequence shown in FIG. 14 in residues 126 through 104 plus 109 through 126. This structure shows the region on the right 74 as an inverted form of the PrP sequence. This was done to take advantage of the five aminoacids which naturally form a loop in order to place hydrophobic pyrene in a corresponding hydrophobic region. Also the valine-valine fragment is essential to beta-sheet formation and so is retained in the sequence. In the figure, green denotes possible mouse variants. The amyloidogenic palindrome region 70 may be changed to SS or SSS/AAA. The central region 72 is a loop sequence with steric constraints, thus it is possible to add tryptophan for steric and fluorescence considerations.

Modifications of the aminoacid sequence such as one or more deletions or insertions are possible as alluded to above, provided that the dendrimer retains its branched loop-turn-loop structure as well as aminoacids essential to beta-sheet formation, and preferably contains an optical reporter.

Figure 10:
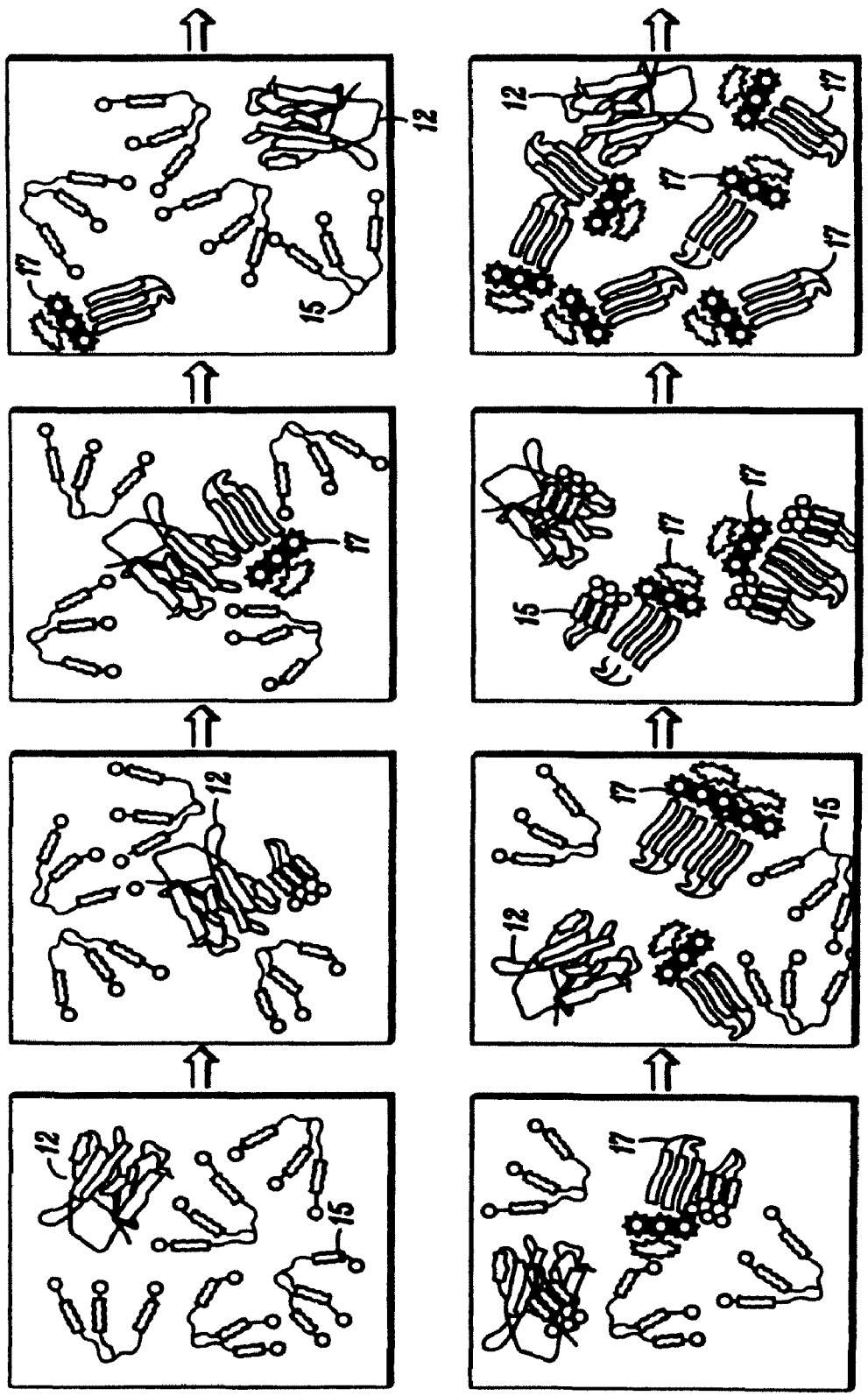
Figure 11A:
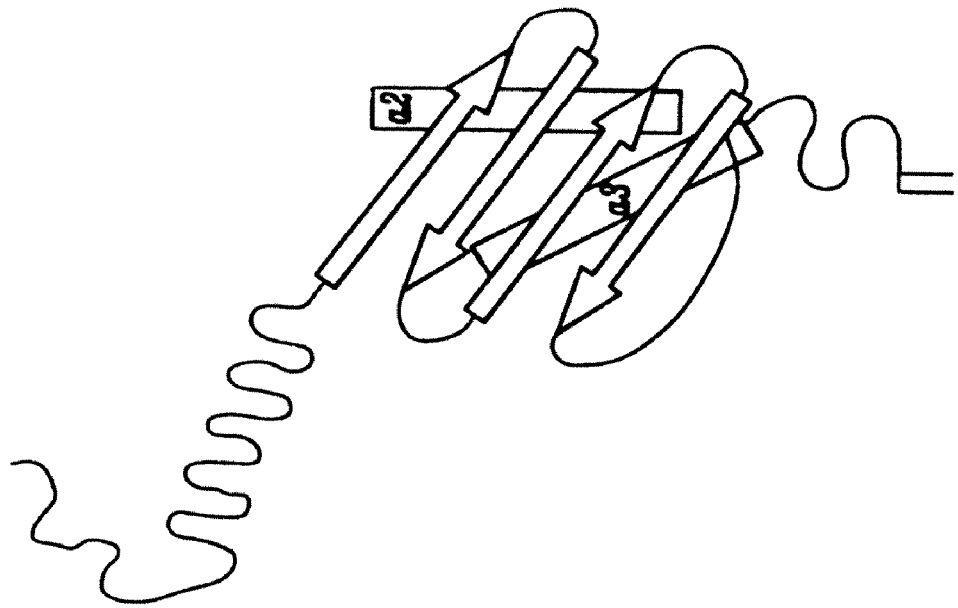
FIG. 11 is a structural diagram of proteins used in the current prior art prion-diagnostic market; wherein FIG. 11a on the left shows the PrPsens protein molecule and FIG. 11b on the right shows a PrPres protein molecule.
Figure 11B:
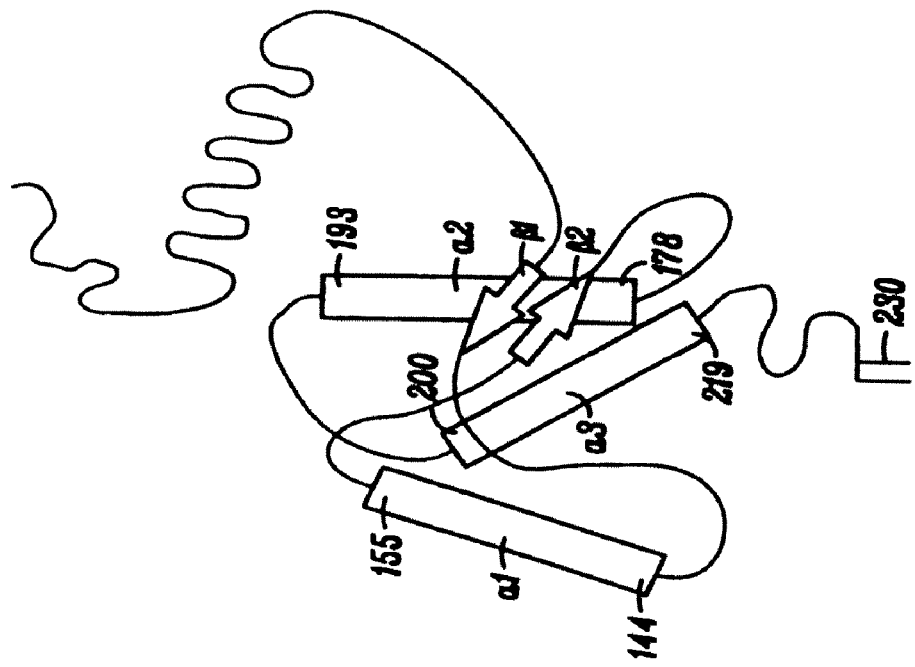

FIG. 10 shows a schematic diagram of how the dendrimer probes 15 amplify signal and propagate conformational change without aggregation and without increasing the biohazard or infectious nature of an abnormal protein or prion test sample 12. The figure shows that once the dendrimer probes 15 come into contact with the abnormal sample 12, the dendrimer probe 15 undergoes the conformational shift to a predominately beta-sheet structure 17. The newly formed beta-rich dendrimer probe 17 nucleates other dendrimer probes 15 to make the same transition. By doing so, any optical signal associated with the dendrimer probe 15 is amplified as more probes 15 shift to the beta-rich state 17.

It is important to note that the minimal detectable concentration of pyrene only provides a number for the peptide probe 14 concentration that can be worked with; but the detection limit of the assay is not dependent on it because it is the resultant of the fluorescent ensemble that is being observed. In other words, the real measurement of interest and the rate limiting step in the analysis is the amount of abnormal e.g. prion protein that need to be present in the sample 20 to initiate a conformer change in the peptide probe 14. Immunoassays are typically sensitive in the picomolar range. Nevertheless, once the conformer change is initiated in a single peptide probe 14, the catalytic propagation of its beta-rich structure allows detection in samples previously considered to have abnormal particles 12 at concentrations too low to detect.

Due to its ability to safely, quickly and noninvasively detect abnormal proteinaceous particles such as misfolded proteins, prions, aggregates and fibrils that may lead to toxic plaque formations, the method of this invention is widely applicable to many industries. By example, some of those industries include the diagnostics markets in animal health and human health, the food industry, pharmaceutics, especially for screening animal by-products, transplant/transfusion and vaccine supplies, research and development in such areas as chemotherapies for TSE's, as well as national security in the area of biosensors for biowarfare agents.

Figure 31:
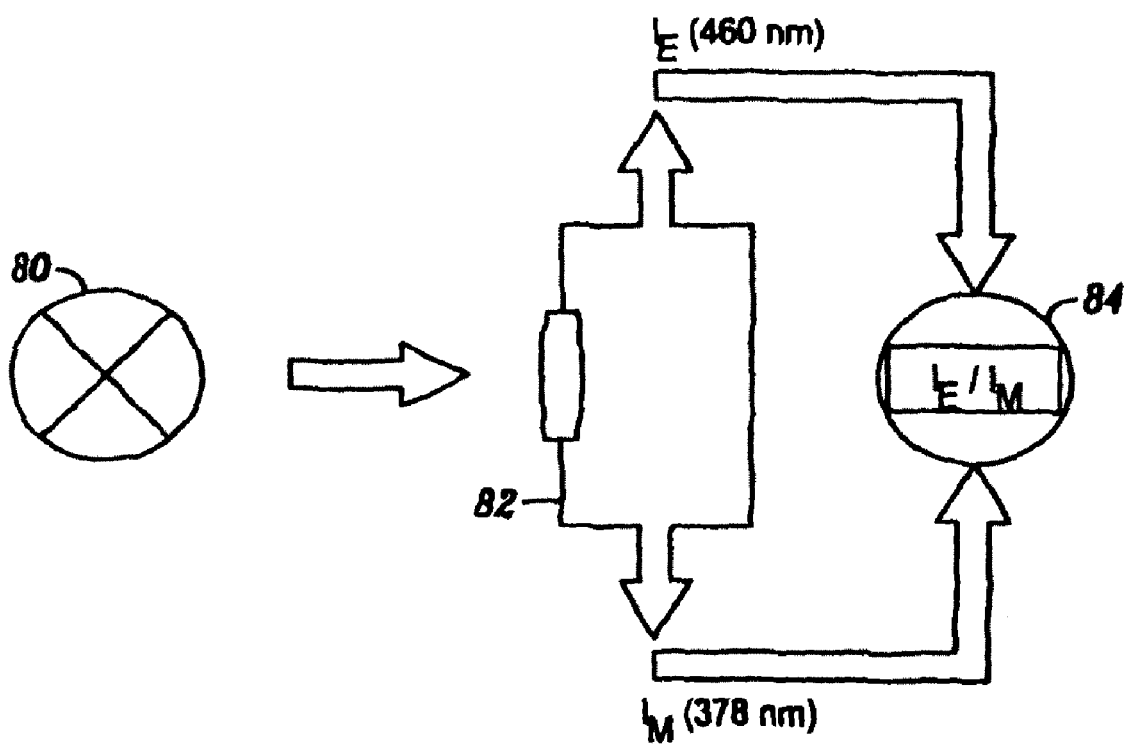
Figure 32:
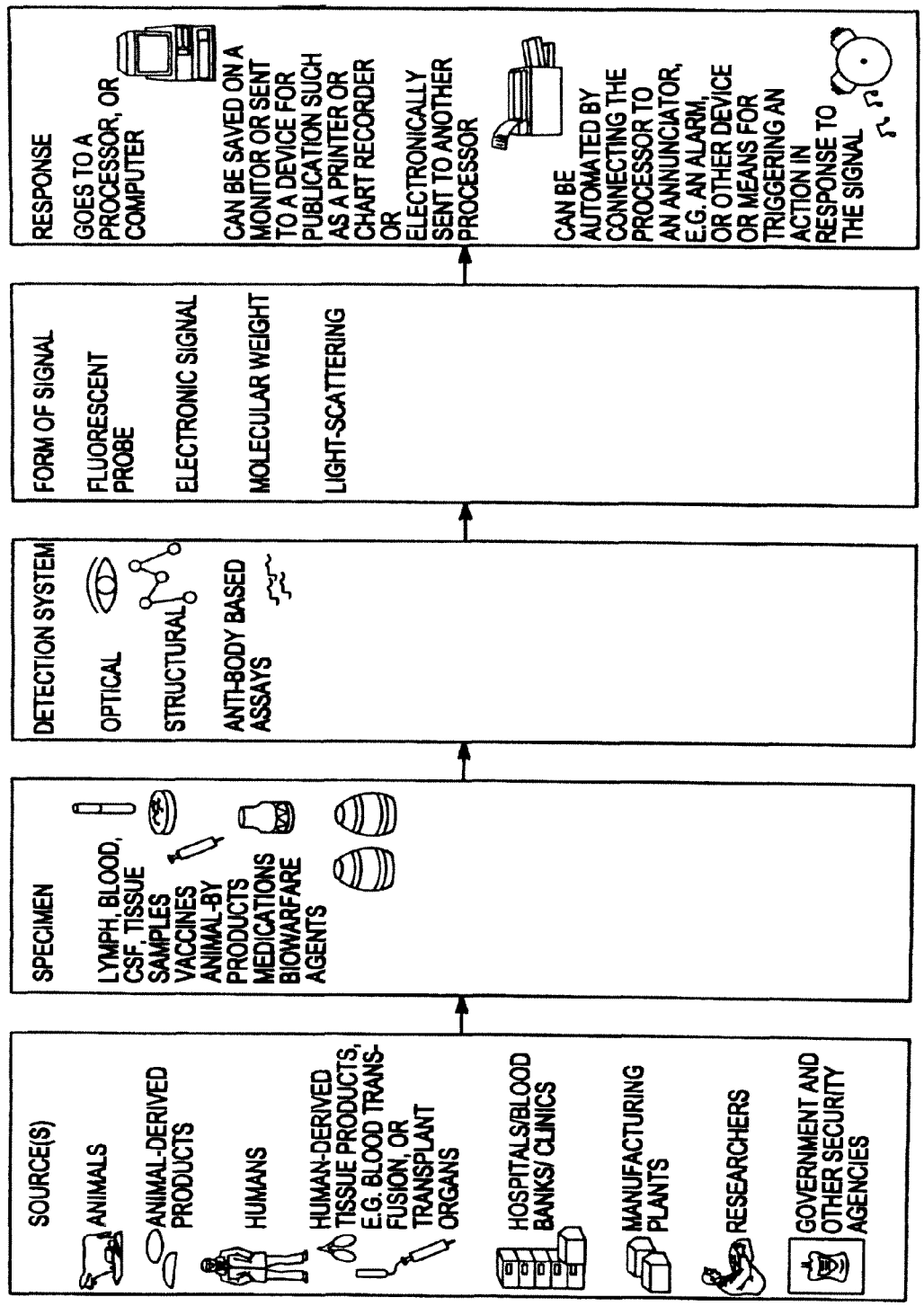

Accordingly, in yet another preferred embodiment of the invention, the methods discussed herein can be applied for use with a simple detection instrument such as the one shown in FIG. 31. The device shown in FIG. 31 is a simple optical device that includes a light source 80 shown in blue e.g. lamp or laser; a T-format sample cell 82 shown in grey; and a photomultiplier tube 84 shown in pink. In certain applications it may be desirable to have the method distributed as an assay that includes such a simple device.

Accordingly, the present invention is not limited to the specific embodiments illustrated herein. Those skilled in the art will recognize, or be able to ascertain that the embodiments identified herein and equivalents thereof require no more than routine experimentation, all of which are intended to be encompassed by claims.

Furthermore, it will be understood that the foregoing disclosure is intended to be merely exemplary, and not to limit the scope of the invention—which is to be determined by reference to the appended claims.

What is claimed is:

1. An in vitro method for detecting a target protein having a predominantly β-sheet secondary structure, comprising:
   forming a mixture by adding a propagation catalyst to a sample suspected of containing a target protein having a predominantly β-sheet secondary structure, wherein the propagation catalyst is a peptide that:
   (i) has a predominantly alpha-helix and/or random coil secondary structure and interacts with protein having a predominantly β-sheet secondary structure;
   (ii) undergoes a conformational shift that results in a decrease in alpha-helix and/or random coil secondary structure and an increase in β-sheet secondary structure upon contact with protein having a predominantly β-sheet secondary structure or upon contact with another such propagation catalyst that has undergone such a conformational shift; and
   (iii) is labeled with an optically detectable moiety;
   allowing the propagation catalyst and any target protein present in the sample to interact; and
   detecting any increase in β-sheet secondary structure in the mixture by detecting the optically detectable moiety, the increase being due, at least in part, to an increase in β-sheet secondary structure of the propagation catalyst, wherein any such increase indicates the presence of target protein in the sample.

2. The method of claim 1, wherein the optically detectable moiety is a fluorophore.

3. The method of claim 2, wherein the fluorophore is selected from the group consisting of tryoptophan, 1-anilino-8-napthalene sulfonate (ANS) and Congo Red stain.

4. The method of claim 1, wherein the peptide is labeled with an optically detectable moiety at each of its N-terminus and its C-terminus.

5. The method of claim 4, wherein the optically detectable moieties at each of the N-terminus and C-terminus have the capacity to interact to form excimers.

6. The method of claim 5, wherein, when the propagation catalyst undergoes said conformational shift, interaction between the optically detectable moieties at each of the N-terminus and C-terminus of the peptide probe results in excimer formation.

7. The method of claim 4, wherein the optically detectable moieties at each of the N-terminus and C-terminus comprise a fluorescence energy transfer (FRET) pair.

8. The method of claim 7, wherein, when the propagation catalyst undergoes said conformational shift, interaction between the optically detectable moieties at each of the N-terminus and C-terminus of the peptide probe results in fluorescence energy transfer (FRET).

9. The method of claim 4, wherein the optically detectable moieties at each of the N-terminus and C-terminus comprise a fluorophore/quencher pair.

10. The method of claim 9, wherein, when the propagation catalyst undergoes said conformational shift, interaction between the optically detectable moieties at each of the N-terminus and C-terminus of the peptide probe results in quenching of the fluorescence of the fluorophore.

11. The method of claim 4, further comprising adjusting a reaction condition to increase or decrease interactions between the optically detectable moieties at each of the N-terminus and C-terminus.

12. The method of claim 11, wherein the reaction condition is selected from the group consisting of: ionic strength of the sample, pH of the sample, concentration of the sample, temperature, and the presence or absence of nucleating agents.

13. The method of claim 4, further comprising modifying the amino acid sequence of the propagation catalyst to increase or decrease interactions between the optically detectable moieties at each of the N-terminus and C-terminus.

14. The method of claim 1, wherein the method further comprises, prior to the step of adding the propagation catalyst to the sample, the step of subjecting the sample to a disaggregation technique.

15. The method of claim 1, wherein the detecting step comprises detecting aggregates comprising the propagation catalyst.

16. The method of claim 1, wherein the target protein is associated with a disease.

17. The method of claim 16, wherein the disease is selected from the group consisting of Alzheimer's Disease, Huntingon's Disease, and prion-associated diseases.

18. The method of claim 13, wherein the target protein is selected from the group consisting of Aβ protein, huntingtin protein, transmissible spongiform, and prion proteins.

19. The method of claim 1, wherein the sample comprises a biological sample from a subject.

20. The method of claim 1, wherein the sample comprises a biological sample from a living subject.

21. The method of claim 1, wherein the sample comprises a biological sample from a human subject.

22. The method of claim 1, wherein the sample comprises blood, lymph, CSF, or tissue.

23. The method of claim 1, wherein the sample comprises a biological sample and a solvent.

* * * * *

UNITED STATES PATENT AND TRADEMARK OFFICE
CERTIFICATE OF CORRECTION

PATENT NO.         : 8,062,895 B2                                                      Page 1 of 1
APPLICATION NO.    : 12/726941
DATED              : November 22, 2011
INVENTOR(S)        : Cindy Orser et al.

It is certified that error appears in the above-identified patent and that said Letters Patent is hereby corrected as shown below:

IN THE SPECIFICATION

Column 4, line 55, please replace "the energy difference between two different" with
-- the energy difference between two different conformational states --.

Column 10, line 66, please replace the formula "Pyr*Pyr=(Pyr_Pyr)*" with
-- Pyr*+Pyr=(Pyr_Pyr)* --.

Signed and Sealed this
Eighth Day of May, 2012

David J. Kappos
*Director of the United States Patent and Trademark Office*